United States Patent [19]
Wilson et al.

[11] Patent Number: 5,646,044
[45] Date of Patent: Jul. 8, 1997

[54] EXPRESSION SYSTEMS FOR THE PRODUCTION OF TARGET PROTEINS IN BACILLUS

[75] Inventors: Charles R. Wilson, Santa Rosa; Maria R. Tang, Fairfield, both of Calif.; Harald Berger, Grevenbroich, Germany; Teresa M. Christianson, Petaluma, Calif.; Dieter Hansen, Langenfeld, Germany

[73] Assignee: Henkel Kommanditgesellschaft auf Aktien, Duesseldorf, Germany

[21] Appl. No.: 397,602

[22] Filed: Mar. 2, 1995

[51] Int. Cl.$^6$ .................. C12N 1/21; C12N 15/75; C07H 21/04; C12P 21/00
[52] U.S. Cl. .................. 435/252.31; 435/69.1; 435/196; 435/198; 435/212; 435/320.1; 536/23.2; 536/24.1; 536/24.2
[58] Field of Search .................. 435/252.31, 69.1, 435/70.1, 71.1, 320.1, 183, 195, 196, 212, 219, 198; 536/23.1, 23.2, 24.1, 24.2; 935/22, 33, 38, 41, 45, 66, 74

[56] References Cited

U.S. PATENT DOCUMENTS

| | | | |
|---|---|---|---|
| 4,724,208 | 2/1988 | Brewer et al. | 435/188 |
| 4,801,537 | 1/1989 | Nagajaran et al. | 435/69.1 |
| 4,904,599 | 2/1990 | Ozaki et la. | 435/252.33 |
| 5,188,956 | 2/1993 | Namori et al. | 435/200 |
| 5,217,878 | 6/1993 | van Eehelen et al. | 435/69.1 |
| 5,231,022 | 7/1993 | Saito et al. | 435/209 |
| 5,254,470 | 10/1993 | Murakasmi et al. | 435/225 |
| 5,340,735 | 8/1994 | Christianson et al. | 435/221 |
| 5,352,604 | 10/1994 | Wilson et al. | 435/221 |
| 5,387,521 | 2/1995 | Ferrari | 435/252.31 |

FOREIGN PATENT DOCUMENTS

| | | |
|---|---|---|
| 0283075 | 9/1988 | European Pat. Off. . |
| 0348814 | 1/1990 | European Pat. Off. . |

OTHER PUBLICATIONS

Jacobs et al. (1985) Nucleic Acids Research 13:8915–8926.
Jacobs M. (1987) Poster T-4, 4th Intn'l., Conf. on Genetics & Biotech of Bacilli, San Diego.
Zuker & Stiegler (1981) Nuclic Acids Research. 9:133–148.
Marinus & Morris (1974) J. Mol. Biol., 85:309–322.
Anagnostopoulos & Spizizen (1961) J. Bacteriol 81, 741–746.
Chang & Cohen (1979) Mol. Gen. Genet. 168, 111–115.
Yanisch-Perron et al. (1985) Gene 33, 103–119.
Delmar et al. (1979) Anal. Biochem 99,316–320.
Guzzo et al. "Cloning of The *Pseudomonas aeruginosa* Alkaline Protease Gene . . . " J Bacteriol. 172(2) 942–948 1990.
VanderLaan et al. "Cloning Cheracterization & Multiple Chromosonal Integraton of a Bacilluis Alkaline Protease Gene" Appl Environ Microbiol. 57(4) 901–909 1991.

*Primary Examiner*—Mindy B. Fleischer
*Assistant Examiner*—Nancy J. Degen
*Attorney, Agent, or Firm*—Wayne C. Jaeschke; Frank S. Chow; Jeffrey S. Steen

[57] ABSTRACT

This invention discloses an expression system which is useful in industrial Bacilli to produce target proteins which include, but are not limited to, alkaline proteases, amylases, cellulases, lipases or other hydrolyases which are normally excreted outside of the host cell.

38 Claims, 25 Drawing Sheets

FIG. 6

Partial DNA Sequence of ATCC 53926 Alkaline Protease Gene

```
                          AvaI
        Ndel*    Primer #1  5'-CGAattctgctggccctcgggacc
5'-catatggatgcaatcctcctgctcctgctgccctcgggacctcttccctgccaggctgaagcggtctattcatactttcga
   gtatacctacgttagaggacgagtaagacgaccggagcccctggagaaaggacgtccgactgctcgccagataagtatgaaagct actgaacatttctaaaacagttattaataaccaaaaatttaaattgtcctccaaaaaataggctaccatataattcattt
tgacttgtaaaagatttgtcaataattattggtttttaaaattaaccaggaggtttttatccggatgtatattaagtaaa RBS
tttttctataataaattaacagaataattggatagattatattattctcctctattaaattattctgaataaagaggagagtga
aaaagatattattaattgtcttattaaccctatctaataataggaagataaattaataagacttattctcctctcact
                                    tctaatataataggaagatCTattaat-5' Primer #2
                  ttgtcttattaacctAGGctaatataa-5' Primer #5
Met → Pre sequence 53926   Primer #8
       attatttaattgtctAGAtaaccttat-5'
gtaatgatgaggaaaagagttttggcttgggatgctgggatgctctgacggcgcttcatgctgcgtgttcacgatgcattcagcgattccgcttct
cattactactcctttctcaaaaccgaaccctacgactgccgaagtacgagcacaagtgctaccgtaagtcgctaaggcgaaga → Pro sequence 53926
gctgctcaaccggcgaaaaatgttgaaaaggattatattgtcggatttaagtcaggagtgaaaaccgcatctgtcaaaaggacatc
cgacgagttggccgcctttttctgccgcttttttacaacttttacaactttcctaataacagcctaaatcagtcctcacttttggcgtagacagttttcctgtag
                                                                                       HaeII
atcaaagagagcggcggaaagtggacaagcagtttagaatcatcaacgcggcaaaagcgaagctagacaaagaagcgct-3'
tagttctctcgccgccctttcacctgttcgtcaaatcttagtagtggcgccgttctgcttctgtctcttcttcgcga
```

FIG. 7

Partial DNA Sequence of ATCC 53926:BLAP ClaI Fusion Gene

```
                    AvaI
5'-ctcgggacctcttcctgccaggctgaagcggtctattcatactttcga
   gagcccctggagaaaggacggtccgactt cgccagataagtatgaaagct actgaacattttctaaaacagttattaataaccaaaaaatttaaatt ggtcctccaaaaaaataggcctaccatataattcatt
tgacttgtaaaagatttgtcaataattatt ggttttttaaaattaaccaggaggttttttatccgatgtgtatattaagtaaa Primer #3  5'-taaattat CTAgaataaagaggaggagag
                                                             RBS
                Primer #6   5'-cttctatttaaaGGatCctgaataaagagg
         Primer #7  5'-atagattataGGatcctt ctatttaaa →
ttttctataataattaacagaataatagattatattatcctctattt aaattattctgaataaagaggagagtga
aaaayatattattaattgtcttataacctt atctaataataataggaagataaattaataagactt attctcctcctcact Met → Pre sequence 53926
gtaatgatgaggaaaaagagtttttggcttgggatgctgacggccttcatgctgctcgtgttcacgatgcatcgcatcggctgct → Pro
cattactactcctttctcaaaaaccgaacctacgactgccggaagtacgagcacaagtgctaccgtagctagccgacga
sequence BLAP                                                            ClaI
gaggaagcaaaagaagcaaaaataattaattggctttaatgagcaggaagctgtcagtgagttgtagaacaagtagaggcaaatgacgag
ctccctcgtttctctttataaattaaccgaaattactcgtccttgacagtcactcaaacatcttgtcatccgttactgctc gtcgccattctctctgaggaagaggaagtcgaaattgaattgcttcatgagttgaaacgattcctgtttatccgttgagttaagc
cagcggtaagagagactcctt cctcagcttccttaacttgctaaggacaaatagg caactcaattcg
                                                                → Mature sequence
ccagaagatgtggacgcgcttgaactt gatccagcgattccttatattgaagaggatgcagaagtaacgacacaatggcgcaatcagtg
ggtctcctacacctgccgaacttgaactagtcgctaaagaataactt cctcacgtctt cattgctgttaccgcgttagtcac
                                                                          TaqI*
BLAP
ccatggggaattagccgtgtgcaagccccggctgccataaccgtgatt gacaggttcctggttaaagttgctgtcccga-3'
ggtaccccttaatcgcggcacgttcggggccgacggtattgcacctaactgtccaagaccacatttcaacgacaggagct
                                                     ←cgttcggggccgacgTCgatt ggcacc-5' Primer #4
```

FIG. 23
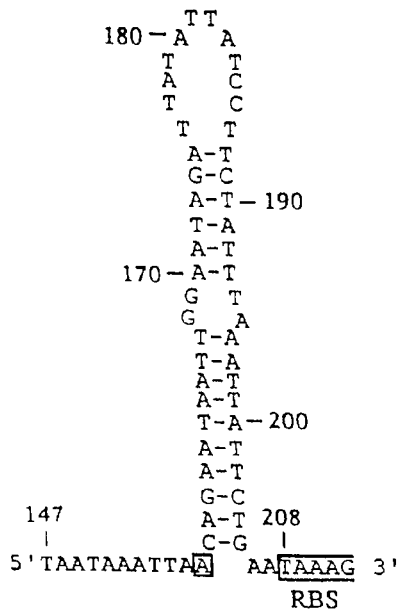
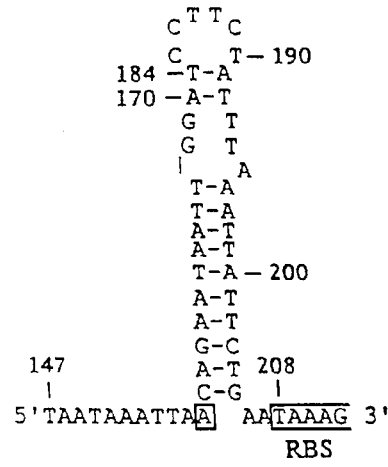
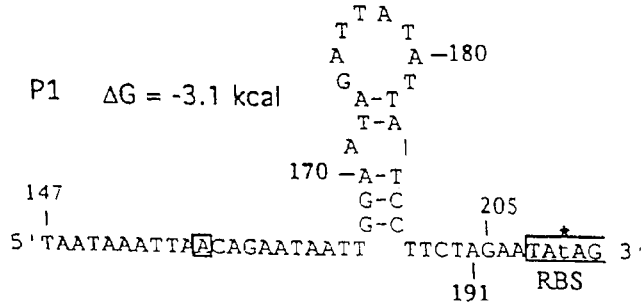
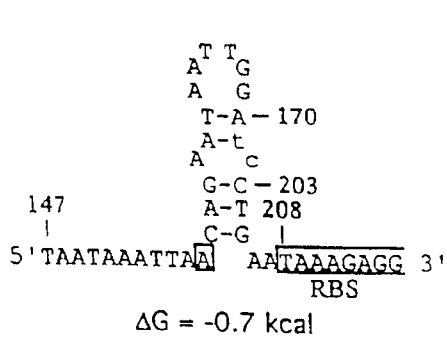

FIG. 24A

DNA Sequence for *Bacillus licheniformis* ATCC 53926
Alkaline Protease Gene and its Controlling Elements

```
   1 CCTCGGGACCTCTTTCCCTGCCAGGCTGAAGCGGTCTATTCATACTTTCG
  51 AACTGAACATTTTTCTAAAACAGTTATTAATAACCAAAAATTTTAAATT
 101 GGTCCTCCAAAAAAATAGGCCTACCATATAATTCATTTTTTTCTATAAT
                     ──►mRNA Start
 151 AAATTAACAGAATAATTGGAATAGATTATATTATCCTTCTATTTAAATTA
                              ──►Pre sequence
 201 TTCTGAATAAAGAGGAGGAGAGTGAGTAATGATGAGGAAAAGAGTTTTT
 251 GGCTTGGGATGCTGACGGCCTTCATGCTCGTGTTCACGATGGCATTCAGC
                ──►Pro sequence
 301 GATTCCGCTTCTGCTGCTCAACCGGCGAAAATGTTGAAAAGGATTATAT
 351 TGTCGGATTTAAGTCAGGAGTGAAAACCGCATCTGTCAAAAGGACATCA
 401 TCAAAGAGAGCGGCGGAAAAGTGGACAAGCAGTTTAGAATCATCAACGCG
 451 GCAAAAGCGAAGCTAGACAAAGAAGCGCTTAAGGAAGTCAAAAATGATCC
                                             ──►Mature
 501 GGATGTCGCTTATGTGGAAGAGGATCATGTGGCCCATGCCTTGGCGCAAA
         Protease
 551 CCGTTCCTTACGGCATTCCTCTCATTAAAGCGGACAAAGTGCAGGCTCAA
 601 GGCTTTAAGGGAGCGAATGTAAAAGTAGCCGTCCTGGATACAGGAATCCA
 651 AGCTTCTCATCCGGACTTGAACGTAGTCGGCGGAGCAAGCTTTGTGGCTG
 701 GCGAAGCTTATAACACCGACGGCAACGGACACGGCACACATGTTGCCGGT
 751 ACAGTAGCTGCGCTTGACAATACAACGGGTGTATTAGGCGTTGCGCCAAG
 801 CGTATCCTTGTACGCGGTTAAAGTACTGAATTCAAGCGGAAGCGGATCAT
 851 ACAGCGGCATTGTAAGCGGAATCGAGTGGGCGACAACAAACGGCATGGAT
 901 GTTATCAATATGAGCCTTGGGGGAGCATCAGGCTCGACAGCGATGAAACA
 951 GGCAGTCGACAATGCATATGCAAGAGGGGTTGTCGTTGTAGCTGCAGCAG
1001 GGAACAGCGGATCTTCAGGAAACACGAATACAATTGGCTATCCTGCGAAA
1051 TACGATTCTGTCATCGCTGTTGGTGCGGTAGACTCTAACAGCAACAGAGC
1101 TTCATTTTCCAGCGTCGGAGCAGAGCTTGAAGTCATGGCTCCTGGCGCAG
```

FIG. 24B

```
1151 GCGTATACAGCACTTACCCAACGAACACTTATGCAACATTGAACGGAACG
1201 TCAATGGCTTCTCCTCATGTAGCGGGAGCAGCAGCTTTGATCTTGTCAAA
1251 ACATCCGAACCTTTCAGCTTCACAAGTCCGCAACCGTCTCTCCAGCACGG
1301 CGACTTATTTGGGAAGCTCCTTCTACTATGGGAAGGTCTGATCAATGTC
1351 GAAGCTGCCGCTCAATAACATATTCTAACAAATAGCATATAGAAAAAGCT
1401 AGTGTTTTAGCACTAGCTTTTCTTCATTCTGATGAAGGTTGTTCAATA
1451 TT
```

5,646,044

EXPRESSION SYSTEMS FOR THE PRODUCTION OF TARGET PROTEINS IN BACILLUS

BACKGROUND OF THE INVENTION

1. Field of the Invention

This invention relates to the development of an expression system which is useful in industrial Bacilli to produce target proteins which include, but are not limited to, alkaline proteases, amylases, cellulases, lipases or other hydrolyases which are normally excreted outside of the host cell.

2. Description of the Prior Art

The DNA sequence of a *Bacillus licheniformis* ATCC 53926 gene encoding a subtilisin Carlsberg type protease has previously been disclosed in European Patent EP0348814 (Jan. 3, 1990) and Jacobs, M. et al. (1985) Nucleic Acids Research 13:8915–8926. This DNA sequence contains a putative stem-loop structure positioned just upstream from the ribosomal binding site (RBS) and the translational initiation codon (FIG. 1). The ΔG of formation of this structure has been calculated to be −16.0 kcal/mole, using the method from Zuker and Stiegler. There was evidence that deletion of a StuI/DraI fragment from the *B. licheniformis* Carlsberg protease gene, which includes an upstream region and most of the stem-loop, affects protease production by altering, the efficiency of mRNA translation (Jacob, M.,(1987) Poster T-4, Fourth International Conference on Genetics and Biotechnology of Bacilli, San Diego, Calif.). When a premoter inducible by xylose($P_{xyl}$) was cloned into the StuI site in front of the stem-loop, protease mRNA synthesis was detected during exponential growth but protease activity was only detected in the stationary phase of growth (Jacob, M.,(1987). This is he same result as for the native Carlsberg promoter($P_{carl}$). When the StuI/DraI fragment was deleted and replaced by a fragment carrying $P_{xyl}$, then Carlsberg protease activity was detected during exponential growth. Similar amounts of full length Carlberg mRNA were detected in the exponential stage of growth for constructs with and without the putative stem-loop structure (Jacob, 1987; data not shown) leading to the conclusion that the effect on protease yield was at the level of translation.

SUMMARY OF THE INVENTION

As described above, the alkaline protease gene from *Bacillus licheniformis* ATCC 53926 contains a putative stem loop structure located within the controlling sequence and encompassing the ribosomal binding site (RBS). The ΔG of formation of this structure has been calculated to be −16.0 kcal/mole, using the method of Zuker and Stiegler, as described below. The present invention relates to the construction of five controlling elements (P1–P5) with different portions of the putative stem loop deleted. The calculated ΔG values of the respective stem loop structures range from +2.0 kcal/mole to −10.9 kcal/mole. According to the present invention, the five altered controlling elements as well as the wild type sequence have been fused to an alkaline protease gene isolated from *Bacillus lentus* (BLAP) and cloned into derivatives of plasmids pCB56C, pCB75C and pCB76C. In addition, constructs have been transformed into strains of *Bacillus subtilis* and *B. licheniformis* and protease production evaluated in shake flasks. We have found that three of the five altered stem loop structures (P2,P4 and P5) produced yields of protease in *B. subtilis* which did not differ significantly from the wild type structure. P 1, whose protease yield in *B. subtilis* was decreased significantly as compared to the wild type, was found to carry a point mutation within the RBS. P3 produced a two-fold increase in protease in *B. subtilis*. In an industrial strain or *B. licheniformis* ATCC 53926, controlling elements P2–P5 all increased protease yield more than eight-fold over the wild type controlling element. The best productivity was associated with construct pCB56C-P3 which showed a 25 fold increase in protease over the control strain of *B. licheniformis* ATCC 53926 carrying pCB56C. The lowest productivity was associated with construct pCB56C-P1 which produced an 8 fold increase in protease over the control strain. These modified controlling elements are useful for increasing the production of extracellular enzymes, typically hydrolases such as proteases, lipases and esterases and also polysaccharide degrading enzymes such as cellulases and amylases.

BRIEF DESCRIPTION OF THE DRAWINGS

FIG. 6. Partial nucleotide sequence of the ATCC 53926 alkaline protease gene extending from an NdeI site downstream to a HaeII site located within the coding region for the mature protease. The complete protease gene is carded on an AvaI/SstI fragment in plasmid pC50 which served as a template for PCR reactions to modify the upstream portion of the stem-loop region. The AvaI site used for cloning is shown as are the primers used for PCR synthesis of the controlling elements with modified stem-loop regions. The new restriction sites in the piers used for the PCR have been underlined. The stem-loop region is designated by the long arrows. The ribosomal binding site and the ATG initiation codon are shown in bold type.

FIG. 7. Partial nucleotide sequence of the ATCC 53926:BLAP protease fusion gene extending from the unique AvaI site downstream to a TaqI site located within the coding region for the mature BLAP protease (SEQ. ID NO. 7). The complete protease gene is carried on an AvaI/SstI fragment in plasmid pCB11C which served as a template for PCR reactions to modify the downstream portion of the stem-loop region. The NcoI site used for cloning is shown as are the primers used for PCR synthesis of the controlling elements with modified stem-loop regions. The new restriction sites in the primers used for cloning have been underlined. The stem-loop region is designated by the long arrows. The ribosomal binding site and the ATG initiation codon are shown in bold type.

Figure 1:
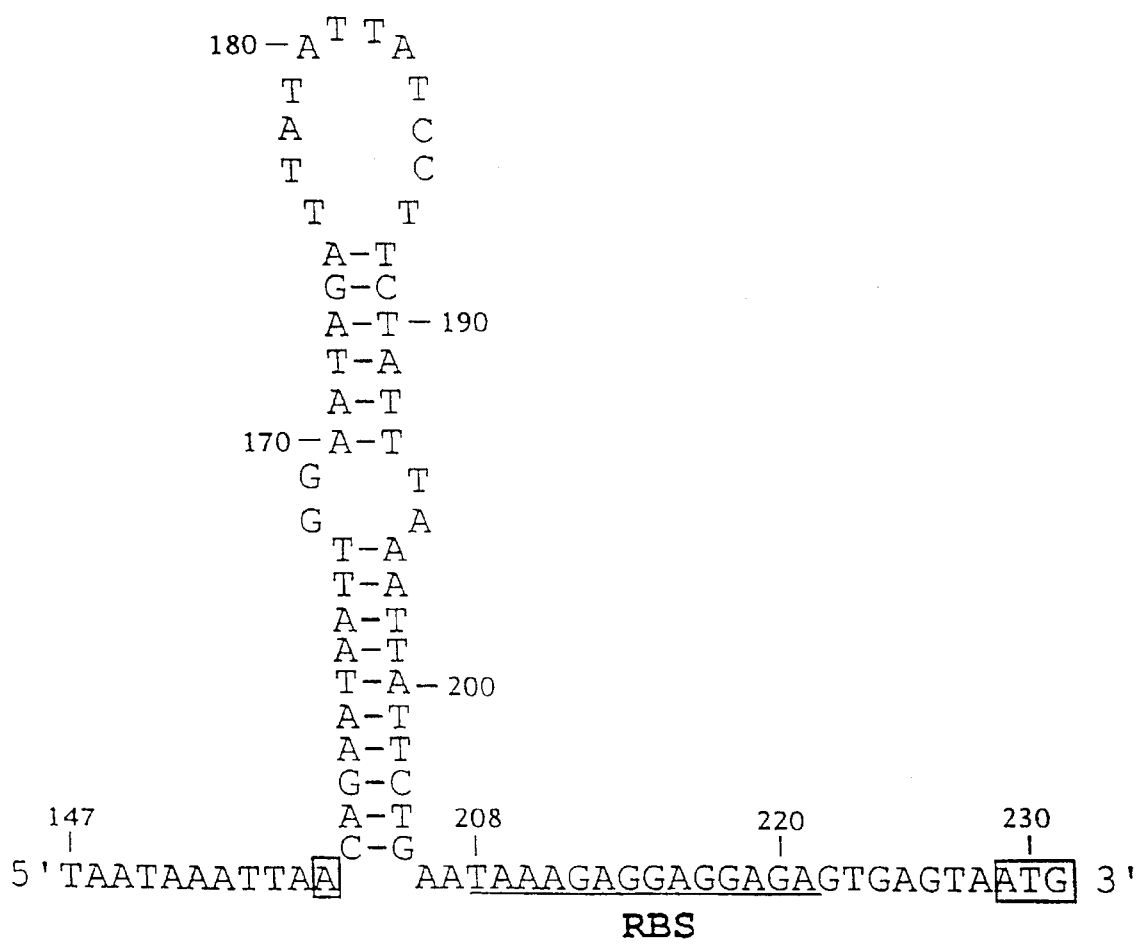
FIG. 1. Shows the putative stem-loop structure (SEQ. ID NO. 1) which can form in the *B. licheniformis* ATCC 53926 alkaline protease gene sequence just upstream from the ribosomal binding site and AUG initiation codon. It is not known if this loop forms within the DNA or after transcription within the mRNA. For convenience of numbering the stem-loop is shown as DNA. The stem-loop has a _G of −16.0 Kcal/mol as calculated by the PC/GENE RNAFOLD program using the method of Zuker, M. and Stiegler, P. (1981)Nuc. Acids Res. 9:133–148.

Protease values were calculated by the AAPF method described in Example 3. Each point on the graph represents the average of either 7 flasks for each strain carrying a P construct or 11 flasks for the pCB56C control strain.

FIG. 23. Potential stem-loop structures predicted to form in the mRNA sequence just upstream from the ribosomal binding site for the B. licheniformis ATCC 53926 alkaline protease gene. The sequences have not been altered by substituting Uracil for Thymine so as to maintain a consistency in the numbering of the nucleotide residues and to make a comparison with FIG. 2 easier. The native sequence is designated as WT for wild type; the P1–P5 deletions are described in FIG. 2 and in Example 5. The free energy calculations associated with each stem-loop structure are also shown. The Adenine at position 239 was identified as the transcriptional start by M. Jacobs (1987) Poster T4, Fourth International Conference on Genetics and Biotechnology of Bacilli.

FIG. 24A and 24B. DNA sequence of a B. licheniformis ATCC 53926 fragment encoding an alkaline Carlsberg-type protease, and its controlling elements (SEQ. ID NO. 8). This sequence has been previously reported in European Patent EP0348814. The transcription start site has been indicated along with the stem-loop structure positioned upstream from the transcription start site. The beginnings of the pre, pro and mature regions of the Carlsberg-type protease.

PREFERRED EMBODIMENTS

In the broadest aspect, this invention relates to modified ATCC 53926 alkaline protease controlling regions which, when placed upstream of a heterologous target gene, such as the gene encoding the Bacillus lentus alkaline protease (BLAP), result in increased production of the target protease when the Bacillus licheniformis host strain is grown when Bacillus licheniformis host strain is grown between pH 7.0 and 9.5 in the temperature range between 34° and 39° C., using an appropriate culture medium as described in Table 1 or in a similar complex medium which contains assimilable carbon and nitrogen sources, and inorganic salts which allow vigorous growth of the microorganism. Major media components may include corn starch, soy meal, sodium caseinate, a brewing residue and corn steep liquor. Minor components may include inorganic components such as ammonium and sodium phosphate. This invention discloses the deletion of portions of a DNA sequence which is believed a stem loop structure just upstream from the ribosomal binding site and translational initiation codon of the ATCC 53926 alkaline protease gene, which result in an increased production of protease as compared to a control strain in which the stem-loop region has not been altered. The construction and cloning of five promoter region alterations (P1–P5) into the Escherichia coli plasmid pUC19 are accomplished by designing oligonucleotide piers, as described for example, in Example 5, which are used to synthesize two DNA fragments by the PCR technique. The, Polymerase Chain Reaction is performed using commercially available GeneAmp™ kits according to the instructions of the manufacturer, Perkin Elmer Cetus (761 Main Avenue, Norwalk, Conn. 06859). Oligonucleotide design allows the two PCR fragments to be cloned into a pUC19 vector in such a way as to reconstitute a modified ATCC 53926 stem loop region. AvaI/NcoI restriction fragments carrying the modified promoter elements (P1–P5) are then ligated to the missing portions of the ATCC 53926:BLAP fusion gene carried on plasmid pMc13C so as to reconstitute a complete 53926:BLAP expression system. An AvaI/SstI fragment carrying the entire modified fusion gene is then cloned into Bacillus vectors which are derivatives of pCB56C, pCB76C or pCB75C.

The second aspect of this invention are Bacillus plasmids which carry the P1–P5 promoter regions joined to the ATCC 53926:BLAP fusion gene with and without the 53926 protease termination sequence. The preferred plasmids for the B. licheniformis ATCC 53926 strain are derivatives of pCB56C and include: pCB56C-P1; pCB56C-P2; pCB56C-P3, pCB56C-P4 and pCB56C-P5. The most preferred plasmid in B. licheniformis is pCB56C-P3. The preferred plasmids for B. subtilis are derivatives of pCB75C and pCB76C and include: pCB75C-P2, pCB75C-P3, pCB75C-P4, pCB76C-P2, pCB76C-P3 and pCB76C-P4. The most preferred plasmids in B. subtills are pCB75C-P3 and pCB76C-P3.

Figure 2:
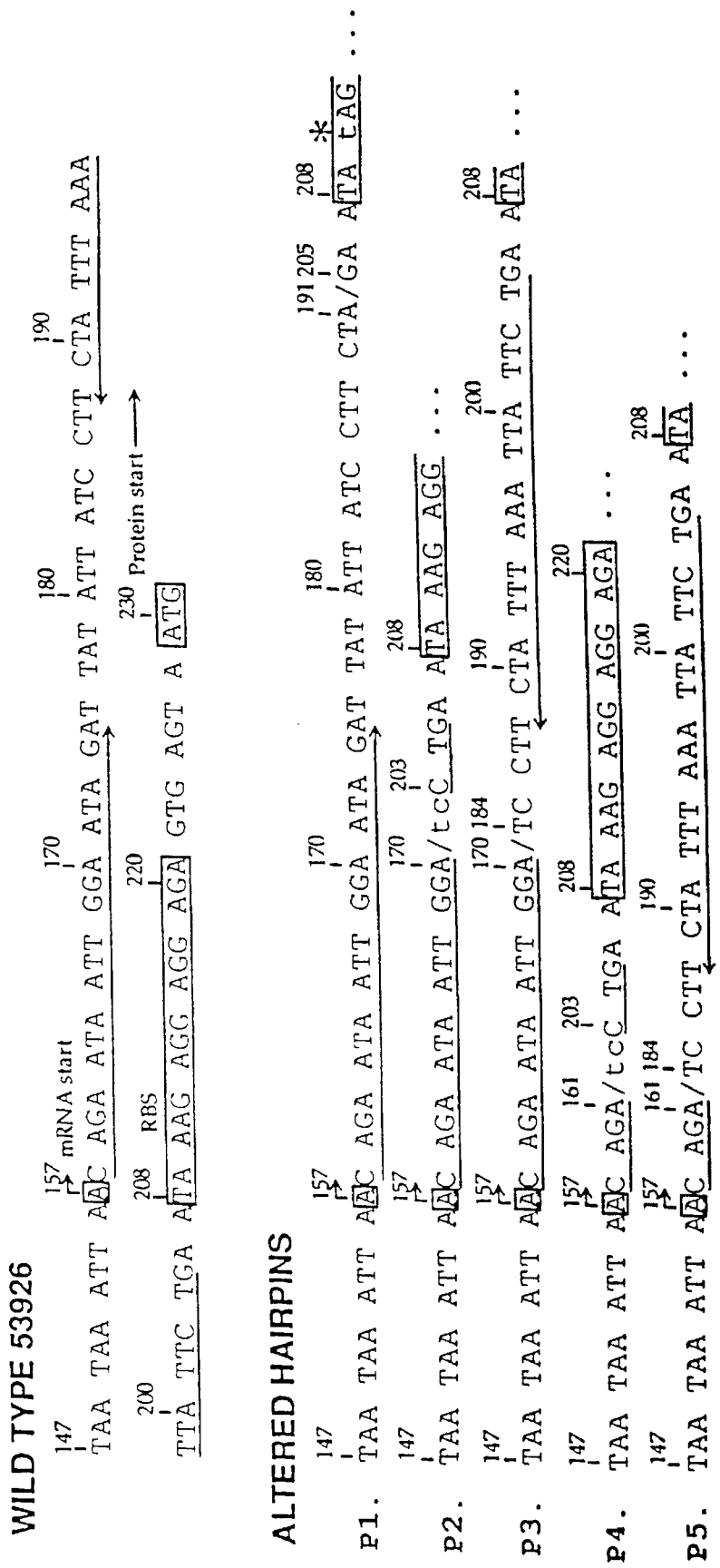
FIG. 2. Shows the alterations of the stem-loop DNA sequence introduced into promoter elements P1–P5 (SEQ. ID NOS. 2–6). The alterations introduced deletions of different portions of the stem loop region using a polymerase chain reactions method described in the text. The numbering of the bases refers to the DNA sequence of the wild type ATCC 53926 alkaline protease gene shown in FIG. 24. The wild type sequence which includes the stem-loop region is also contained within the DNA sequences shown in FIGS. 6 and 7.

The third aspect of this invention are Bacillus strains carrying the aforementioned plasmids. Preferred B. subtilis strains include wild-type industrial production strains. Preferred B. licheniformis strains include industrial production strains of which one example is the B. licheniformis ATCC 53926 strain developed by Henkel. See U.S. Pat. No. 5,352, 604 hereby incorporated by reference. Accordingly, the present invention relates to DNA sequence which controls the expression of a target gene, which extends from nucleotide 1 to nucleotide 312 as shown in FIG. 24 and which includes the ATCC 53926 alkaline protease promoter region, modified stem-loop region, ribosomal binding site, initiation codon and the pre region of the 53926 alkaline protease gene, where the stem-loop region has been modified by deleting at least one base between nucleotide 161 and 203 on the ATCC 53926 DNA sequence as shown in FIGS. 2 and 24.

DEPOSIT OF ORGANISMS

Living cultures of the following have been accepted for deposit under the Budapest Treaty on the International Recognition of the Deposit of Microorganisms for the purposes of patent procedure by the American Type Culture Collection, 12301 Parklawn Drive, Rockville, Md. 20852. The date of deposit is Dec. 21, 1994. The accession number precedes each deposit description:

ATCC 53926 Bacillus licheniformis ATCC 53926, an industrial strain for the production of protease, which was deposited for U.S. Pat. No. 5,340,735.

ATCC 69723 Bacillus licheniformis ATCC 53926 strain which contains plasmid pCB56C-P3. This derivative of plasmid pBC16 carries a ATCC 53926:BLAP Cla fusion gene in which the stem-loop in the controlling region has been modified as shown in FIG. 2.

ATCC 69725 Bacillus subtills SB202 which contains plasmid pC50, which was constructed by cloning a 1.8 kb Sau3A fragment can-ying the alkaline protease gene from B. licheniformis ATCC 53926 into the BamHI site present on plasmid pBC16.

ATCC 69724 Escherichia coli GM33 strain which contains plasmid pCB11 C, which is an ampicillin resistance derivative of Pharmacia plasmid pTZ19R carrying the ATCC 53926:BLAP Cla fusion gene. The genotype of the GM33 strain is dam3 (dam-methylase minus) (Marinus, M. G., and Morris, N. R. (1974), J. Mol. Biol., 85:309–322).

These deposits will be maintained throughout the life of this patent.

The following Examples are included by way of illustration and not by way of limitation.

EXAMPLE 1

Methods and Materials

Bacterial Strains

Bacillus subtills DB104 has the genotype: his, nprR2, nprE18, and aprA3. This strain was obtained from Dr. Roy Doi, University of California at Davis, and has only been used for research purposes. Alternatively, a strain equivalent to DB104 can be derived by deleting the kanamycin resistance plasmid pGR71 from *B. subtilis* strain DB105 (aprE-, hisH, nprE1, nprR2 and KmR). *B. subtilis* DB105 is available as strain 1E51 from the Bacillus Genetic Stock Center, The Ohio State University, 484 West Twelfth Avenue, Columbus, Ohio 43210). *Bacillus licheniformis* ATCC 53926 is an industrial production strain developed at Henkel KGaA, Düsseldoff, Germany. Competent *B. subtilis* cells were prepared and transformed as described by Anagnostopoulos, C. and Spizizen, J. (1961) J. Bacteriol. 81, 741–746. Competent *Escherichia coli* DH5α cells were purchased from Life Technologies, Inc., Gaithersburg, Md. and transformed with plasmid DNA according to manufacturers instructions. Selection for ampicillin transformants was on luria agar plates containing 50 µg/ml ampicillin. Selection for tetracycline resistant transformants was on luria agar plates containing 15 µg/ml tetracycline. Selection for kanamycin resistant transformants was on luria agar containing 20 µg/ml kanamycin. Transformation of *B. licheniformis* was accomplished by using the protoplasting technique as described by Chang, C., and Cohen, S. N., (1979) Mol. Gen. inet. 168, 111–115.

Plasmids

Plasmid pUC19 is a small *E. coli* plasmid (2686 bp) containing parts of plasmids pBR322 and M13mp19 and encoding resistance to ampicillin (Yanisch-Perron et al. (1985), Gene 33, 103–119). It carries a 54 bp multiple cloning site with recognition sites for 20 different restriction enzymes and was purchased from New England Biolabs Inc., Beverly, Mass.

Plasmid pBC16 (4630 bp) is multi-copy, encodes tetracycline resistance and is commonly used as a cloning vector in Bacillus and other gram positive microorganisms.

Plasmid pUB110 (4548 bp) is multi-copy, encodes resistance to both kanamycin and bleomycin and is used as a cloning vector in both Bacillus and Staphylococcus.

Figure 3:
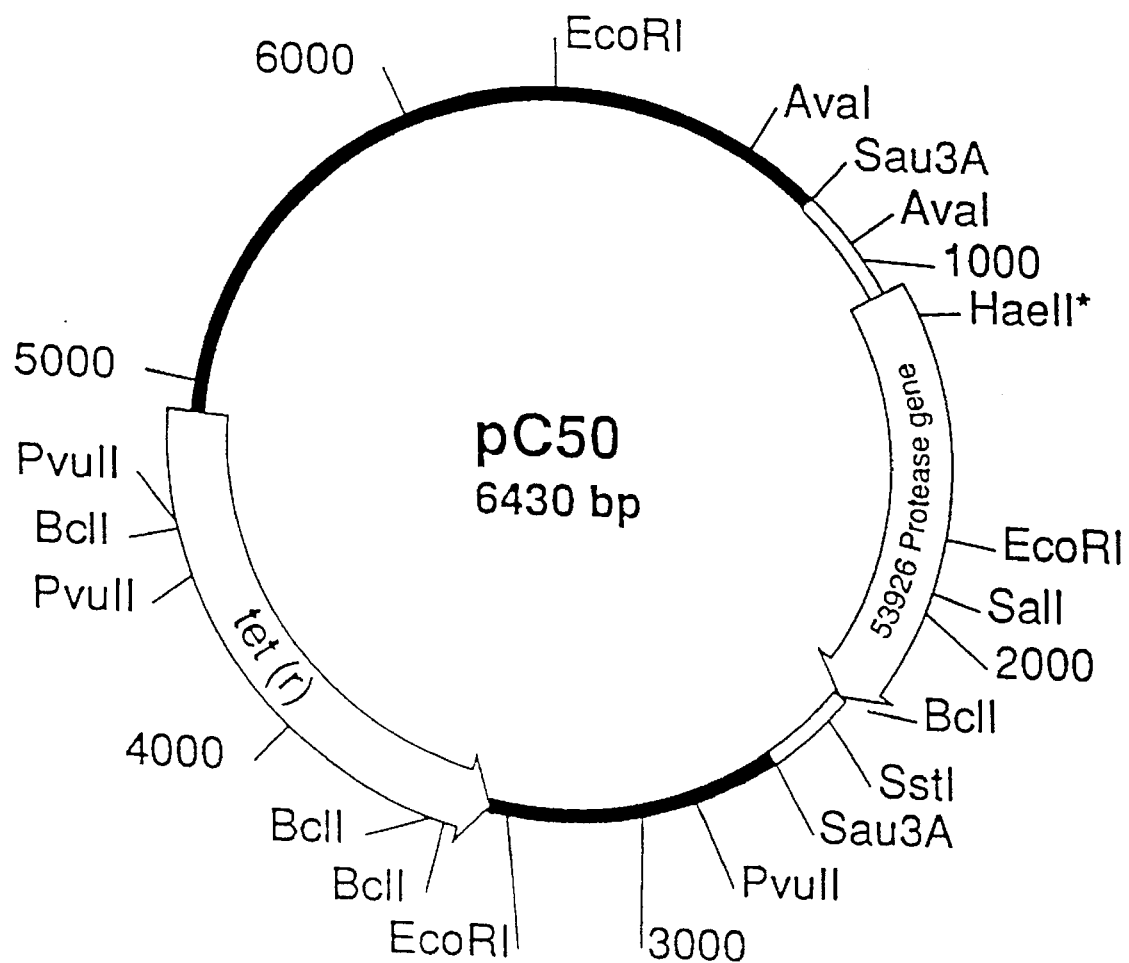
FIG. 3. Shows a restriction map of plasmid pC50 which was constructed by cloning a 1.8 kb Sau3A fragment carrying the alkaline protease gene from *B. licheniformis* ATCC 53926 into the BamHI site present on tetracycline resistance plasmid pB C 16.

Plasmid pC50 was constructed by cloning a 1.8 Sau3A fragment carrying the alkaline protease gene from *B. licheniformis* ATCC 53926 into the BamHI site present on tetracycline resistance plasmid pBC16. A restriction map of pC50 is shown in FIG. 3.

Figure 15:
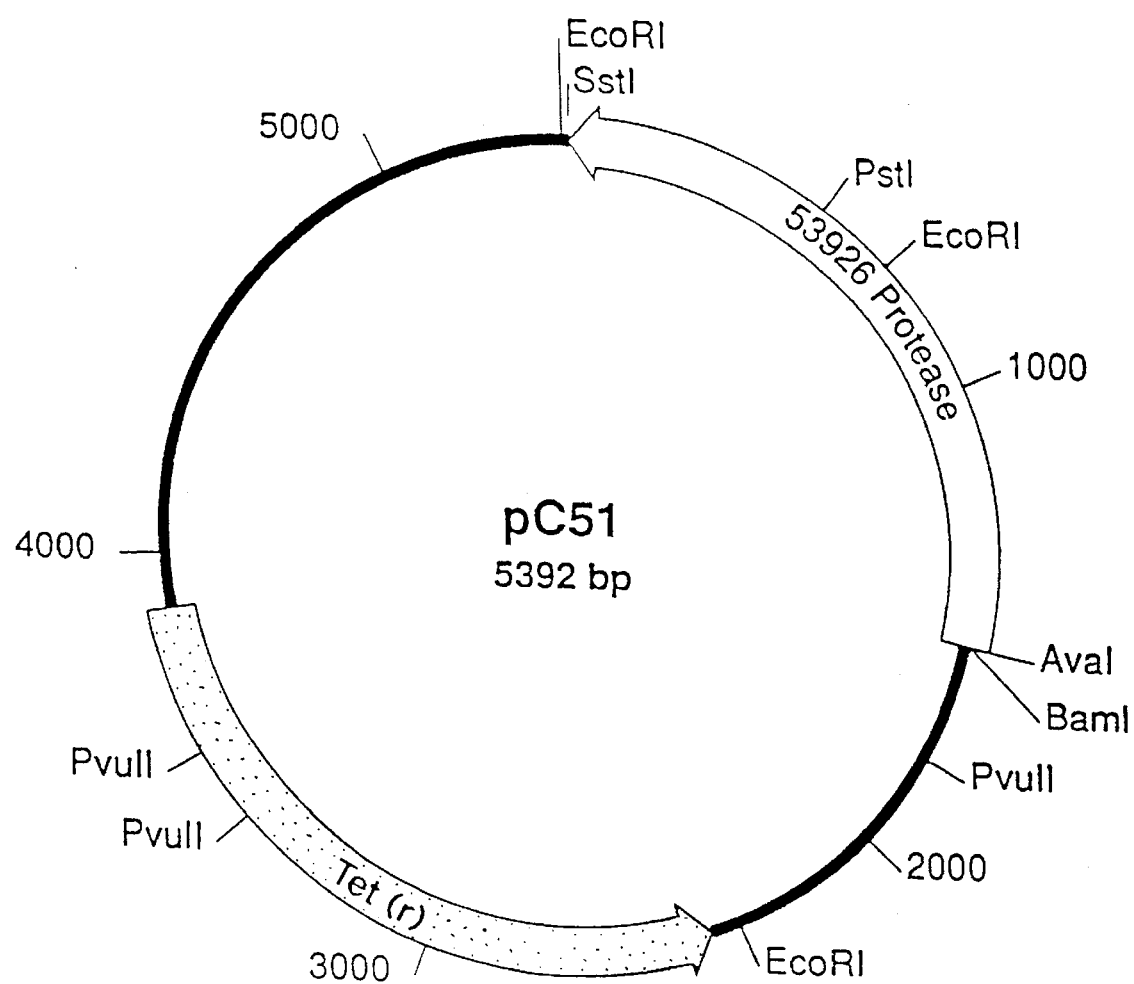
FIG. 15. Shows a restriction map of plasmid pC51 which was constructed by first cloning the ATCC 53926 protease gene from pC50 on a 1.5 kb AvaI/SstI fragment into AvaI/SstI digested pUC19 to form plasmid pH9. Then the 53926 protease gene was removed from pH9 on a BamHI/EcoRI fragment and cloned into BamHI/EcoRI digested pBC16 to form pC51.

Plasmid pC51 was constructed in two steps. First, the 53926 protease gene was removed from pC50 on a 1.5 kb AvaI/SstI fragment and cloned into AvaI/SstI digested pUC19 to form plasmid pH9. Then the 53926 protease gene was removed from pH9 on a BamHI/EcoRI fragment and cloned into BamHI/EcoRI digested pBC16 to form pC51 (FIG. 15).

Figure 16:
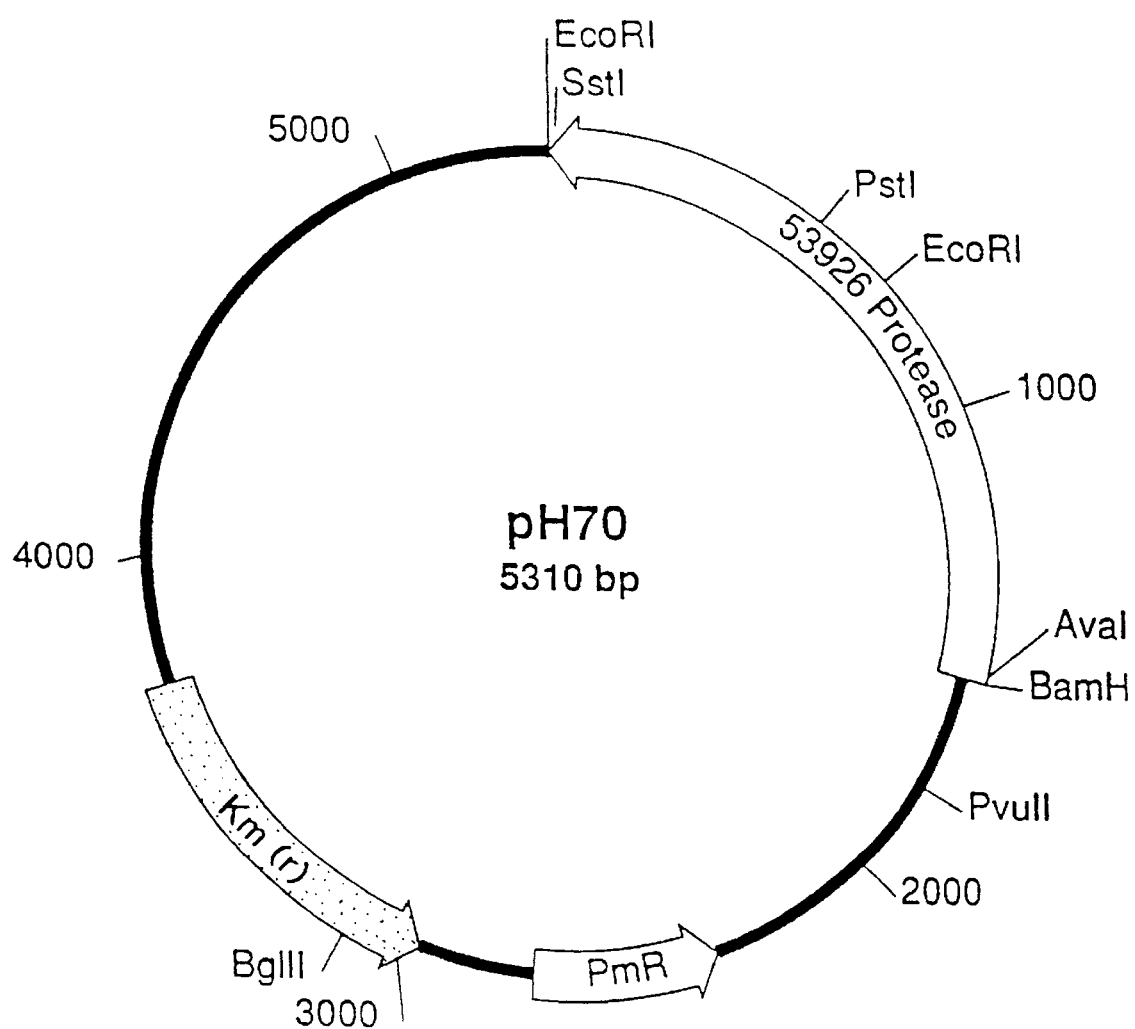
FIG. 16. Shows a restriction map of plasmid pH70 which was constructed by removing the ATCC 53926 protease gene from pH9 on a BamHI/EcoRI fragment and cloning it into BamHI/EcoRI digested pUB110.

Plasmid pH70 was constructed by removing the 53926 protease gene from pH9 on a BamHI/EcoRI fragment and cloning it into BamHI/EcoRI digested pUB110 to form pH70 (FIG. 16).

Plasmid pMc13C (FIG. 4) is a chloramphenicol resistance derivative of plasmid pMc5-8 that contains the 53926:BLAP Cla fusion gene followed by a 164 bp KpnI fragment which includes the 53926 transcription terminator sequence.

Figure 5:
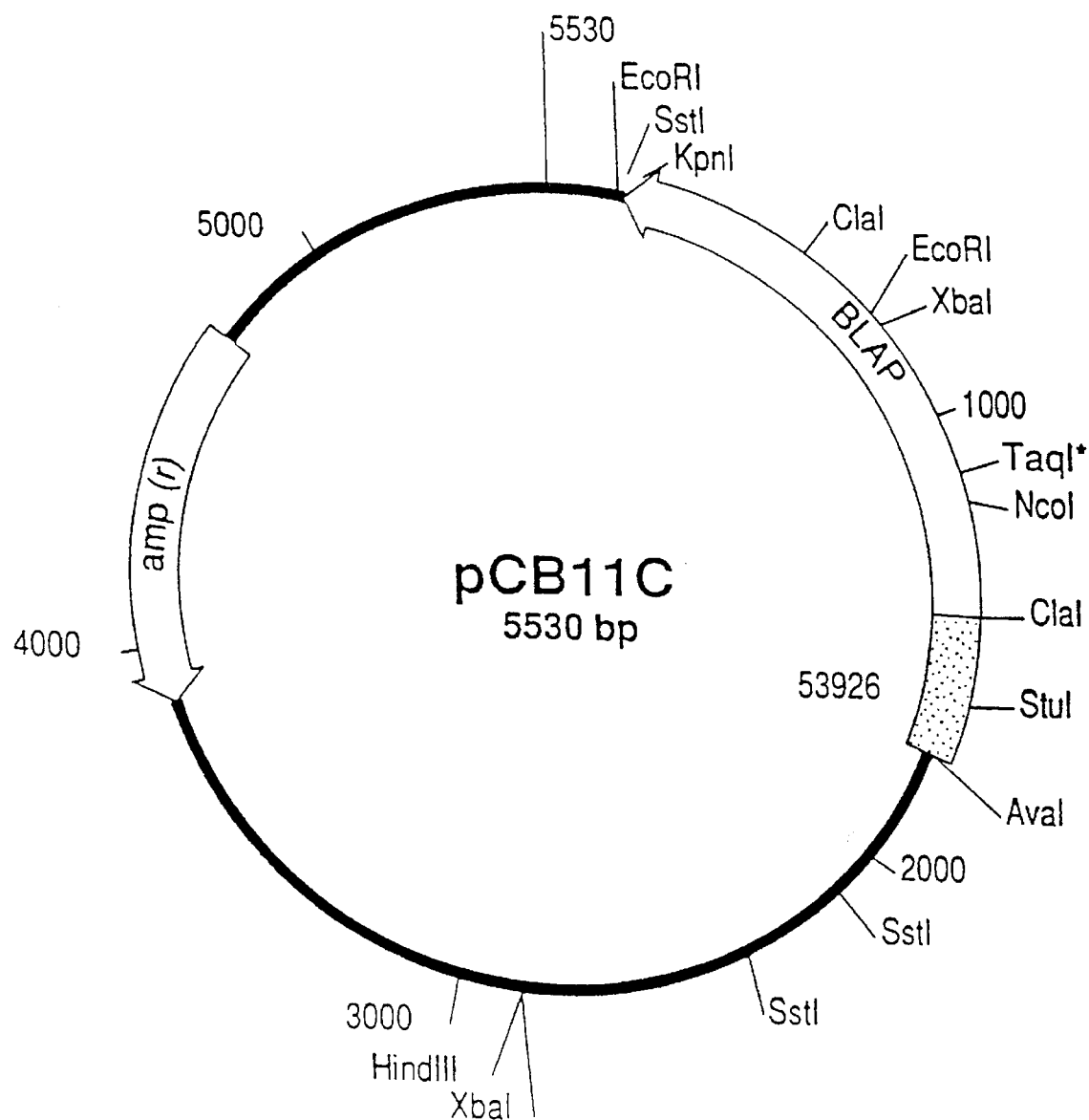
FIG. 5. Shows a restriction map of plasmid pCB 11C which is an ampicillin resistant derivative of Pharmacia plasmid pTZ 19R (Pharmacia Biotech, Inc., Alameda, Calif.) which contains a hybrid fusion between the *B. licheniformis* ATCC 53926 protease gene and the *B. lentus* DSM 5483 BLAP gene. Specifically, this hybrid fusion contains DNA encoding the promoter, ribosomal binding site, and 21 residues of the pre sequence from the ATCC 53926 alkaline protease gene (P-53926) fused to a DNA sequence encoding the last five residues of the BLAP pre sequence and all of the pro and mature residues of BLAP. This fusion is referred to as the ClaI fusion because this restriction site is located at the juncture between the ATCC 53926 and DSM 5483 DNA's.

Plasmid pCB11C is an ampicillin resistant derivative of Pharmacia plasmid pTZ19R (Pharmacia Biotech, Inc., Alameda, Calif.) which contains a hybrid fusion between the *B. licheniformis* ATCC 53926 protease gene and the *B. lentus* DSM 5483 BLAP gene, as shown in FIG. 5. Specifically, this hybrid fusion contains DNA encoding the promoter, ribosomal binding site, and 21 residues of the pre sequence from the ATCC 53926 alkaline protease gene (P-53926) fused to a DNA sequence encoding the last five residues of the BLAP pre sequence and all of the pro and mature residues of BLAP. This fusion is referred to as the ClaI fusion because this restriction site is located at the juncture between the ATCC 53926 and DSM 5483 DNA's.

Plasmid pCB13C was derived from pCB11C by inserting a 164 bp KpnI fragment carrying the transcription terminator (T-53926) from the ATCC 53926 alkaline protease gene at the KpnI site downstream from the BLAP terminator.

Plasmid pCB56C was constructed by ligating the AvaI/SstI fragment from pCB13C, which carries the 53926:BLAP Cla fusion gene and 53926 transcription terminator, to the AvaI/SstI vector fragment from pC51.

Plasmid pCB75C was constructed by ligating the AvaI/SstI fragment from pCB11C, which carries the 53926:BLAP Cla fusion gene, to the AvaI/SstI vector fragment from pH70.

Plasmid pCB76C was constructed by ligating the AvaI/SstI fragment from pCB13C, which carries the 53926:BLAP Cla fusion gene and 53926 transcription terminator, to the AvaI/SstI vector fragment from pH70.

DNA Sequences

The DNA sequence of a NdeI/HaeII fragment from pC50 which contains the promoter stem-loop region, ribosomal binding site and translational initiation codon of the 53926 alkaline protease gene is shown in FIG. 6. The DNA sequence from pCB11C which includes the ATCC 53926:BLAP Cla fusion gene from just upstream of the AvaI site in 53926 to a TaqI site just downstream from the unique NcoI site present within the sequence for mature BLAP is shown in FIG. 7.

EXAMPLE 2

HPLC Purification of DNA Fragments

Purification of DNA restriction fragments was achieved by HPLC chromatography. The 1550 bp AvaI/SstI DNA fragment containing the ATCC 53926 protease gene was separated from the 3800 bp AvaI/SstI vector DNA fragment using a Waters HPLC with a GenPak Fax HPLC column. Chromatography conditions were: Buffer A: 25 mM Tris-HCl pH 8, 1 mM EDTA; Buffer B: as for buffer A but with 1M NaCl; Flow rate 0.8 ml/min, 2700 psi; Gradient 55% to 75% buffer B in 45 min. The peak at 15 min contained the 1550 bp DNA fragment, while the peak at 17 min contained the 3800 bp DNA fragment, as could be shown by gel electrophoresis of collected fractions. Amounts of the large AvaI/SstI vector DNA fragments from both pC51 and pH70 sufficient for cloning were isolated by this method.

EXAMPLE 3

Protease Measurements

Protease was determined either by our HPE method using casein as a substrate which follows or by measuring paranitroaniline release from the synthetic peptide substrate N-succinyl-L-Ala-L-Ala-L-Pro-L-Phe-p-nitroanilide (AAPF paranitroanilide) (SEQ. ID NO. 9).

HPE Assay

Protease production of the ATCC 53926 promoter routants present in pCB75C and cloned into *B. subtilis* were analyzed using the HPE assay. The HPE assay was adapted from the Mikro-HPE Methode aus der Methodensanunlung der Biotechnologie-Abteilung, Henkel KGaA. This is a discontinuous assay using casein as the substrate. Rate of casein degradation by a protease is measured by monitoring the release of acid-soluble peptide fragments as a function of time. Acid-soluble peptides are quantified spectrophotometrically at 290 nm. The result is expressed in HPE (Henkel Protease Einheit, Henkel protease unit). Proteolytic activity was determined with the HPE assay using casein as a substrate. The final concentrations of the substrate solution were 12 mg.ml$^{-1}$ of casein (prepared according to Hammarsten; Merck Darmstadt, #2242) and 30 mM Tris in synthetic tap water. Synthetic tap water is a solution of 0.029% (w/v) $CaCl_2.2H_2O$, 0.014% (w/v) $MgCl_2 \cdot 6H_2O$, and 0.021% (w/v) $NaHCO_3$. The substrate solution is heated to 70° C. and pH is adjusted to 8.5 at 50° C. using 0.1N NaOH. The protease solution is prepared by dilution in 20 mM MES pH 5.8. In 2.2 ml Eppendoff tubes 750 µl of casein substrate is added to each tube in 15 second intervals and allowed to equilibrate for 10 min before initiating the assay. The assay is initiated by the addition of enzyme solution in the same time interval as that of the substrate addition and incubated at 50° C. for 15 min. The reaction is terminated by the addition of 600 µl of 0.44M trichloroacetic acid (TCA), 0.22M sodium acetate in 3% (v/v) glacial acetic acid. After cooling on ice for 15 min the TCA-insoluble protein is removed by centrifugation for 8 min in an Eppendorf table-top centrifuge at maximum speed. Then 900 µl of the supernatant is mixed with 300 µl of 2N NaOH in a 1.5 ml Eppendoff tubes and absorbance of this mixture, containing TCA-soluble peptides, is recorded at 290 nm.

Chromoenic Substrate AAPF-pNa Assay

A peptide derivative; N-succinyl-L-Ala-L-Ala-L-Pro-L-Phe-p-nitroanilide (AAPF-pNA) (SEQ. ID NO. 9) was used as the substrate in this assay which was chosen to analyze protease production in transformants of *B. licheniformis*. The AAPF assay was chosen over the HPE assay because it is easier to perform. This assay method was adapted from DelMar, E. G., Largman, C., Brodrick, J. W., Geokas, M. C. (1979) Anal. Biochem. 99, 316–320. Proteases cleave the amide bond of the peptide derivative between phenylalanine and p-nitroaniline. The appearance of p-nitroaniline is monitored spectrophotometrically at 410 nm and the rate of appearance of p-nitroaniline is a measure of proteolytic activity. Dilutions of the protease broth samples are prepared with 50% (v/v) 1,2-propanediol (propylene glycol) in 100 mM Tris, adjusted to pH 8.6 with 2N HCl. Diluted samples were stable for at least 6 hr. at room temperature. The dilutions are left at room temperature for 10 min. before analysis with the AAPF-pNA (SEQ. ID NO. 9) assay to allow for equilibration of the dilution in the propylene glycol buffer mix. A stock solution of 160 mM AAPF-pNA (SEQ. ID NO. 9) was prepared in dimethylsulfoxide dried over molecular sieve beads (Aldrich; 4–8 mesh, 4 Angstrom) for at least 24 hr. prior to use. Fixed point assays are performed at 25° C. with 1.00 ml of 100 mM Tris, adjusted to pH 8.6 with 2N HCl before being placed in a semimicro cuvette and incubated for 10 min in a waterbath set at 25° C. Ten microliters of the 160 mM AAPF-pNA (SEQ. ID NO. 9) (BACHEM Feinchemikalien, product L-1400) stock is added to the 1.0 ml buffer solution for a final concentration of 1.6 mM and mixed well. Thorough mixing for several seconds of the substrate solution in the Tris buffer is required due to the DMSO (dimethylsulfoxide). The cuvette is transferred to the spectrophotometer and 10 µl of the protease broth dilution is added and mixed well, but no longer than 6 to 7 seconds. The substrate was added to the assay buffer 1 min prior to the assay initiation and the reaction was started by addition of enzyme solution. The protease activity is measured as U/ml and the average is calculated from three fixed point assays for each sample.

EXAMPLE 4

Statistical Analysis of Protease Production

Protease production of the promoter mutants and the wild type strains was compared using a statistical significance test. The z Test for Measurements (zM test) compares a random sample of one or more measurements with a large parent group whose mean and standard deviation is known. Data required for the zM test; n=number of measurements in the sample, m=mean of the sample measurements, M=mean of the large parent group, and S=standard deviation of the large parent group. The following formula was used to calculate z:

$$z = \frac{\sqrt{n} \cdot |M - m|}{S}$$

Interpretation of the z value was adapted from E. S. Pearson and H. O. Hartley, Biometrika Tables for Statisticians, Vol. 1, Table 4 (CUP, 1966). If z is less than 1.96 the probability (P) of encountering a sample mean of m by chance from a parent group whose mean is M and whose standard deviation is S, is to be expected on more than 5% of occasions. In this case, a significant difference is not proven. If z is 1.96 or more, P=5% or less, the difference may be significant. If z is 2.58 or more, P=1% or less, the difference between the means is statistically significant.

EXAMPLE 5

Construction of Altered ATCC 53926 Stem-Loop Structures

Promoter mutations were designed to decrease the stability of the putative stem loop structure located just upstream from the initiation codon for the *B. licheniformis* ATCC 53926 alkaline protease gene hereafter referred to as the 53926 protease gene or just the 53926 gene. All constructions involved PCR amplification of two DNA fragments, one from an upstream region and extending into the stem-loop structure and the second from a restriction site within that part of the gene encoding the mature protease and extending upstream into the stem-loop. The oligonucleotides used in the amplification are shown in FIGS. 6 and 7. The design of the oligonucleotides introduced unique restriction sites at both ends of the PCR fragments. The upstream fragment had a unique AvaI site at its 5' end and either a XbaI, BamHI or a BglII site at its 3' end. The position for introducing the 3' unique sites was chosen so as to delete portions of the stem-loop. The downstream PCR fragment had an XbaI or BamHI site at its 5' end and a PstI site at its 3' end. The 5' sites were also chosen so as to delete a portion of the stem-loop. The altered sequence in the stem-loop region associated with each of the five constructs is depicted in FIG. 2.

Figure 9:
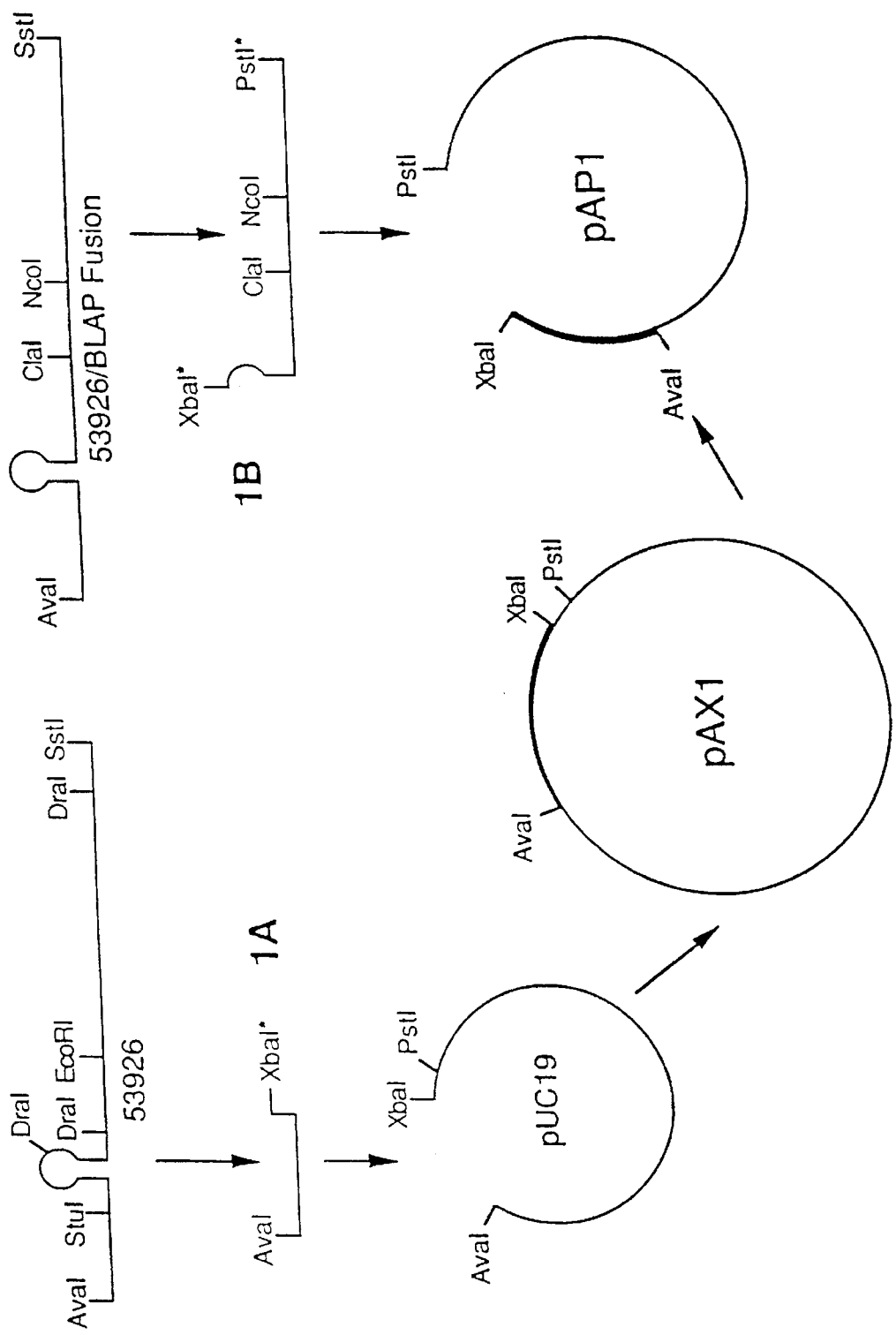
FIG. 9. Strategy for construction of the modified P1 controlling element. The polymerase chain reaction (PCR) fragments are designated 1A and 1B. Plasmid pAP1 contains the ATCC 53926:BLAP fusion gene from the AvaI site past the NcoI site in the coding region for mature BLAP. The two XbaI sites and the PstI site were created for cloning purposes during the PCR synthesis of fragments 1A and 1B. A detailed description of 1A and 1B is given in the text.

Plasmid pAP1 was constructed by ligating PCR fragments 1A and 1B into pUC19. A construction scheme is shown in FIG. 9. DNA fragment 1A was synthesized by PCR using oligonucleotides #1 and #2 (FIG. 6) as primers and plasmid pC50 as a template. It was designed to contain an AvaI site at the 5' end and a XbaI site at its 3' end.

Oligonucleotide #1 included the AvaI site already present in the 53926 protease gene sequence shown in FIG. 6, while oligonucleotide #2 introduced a new XbaI site. After restriction with AvaI and XbaI the 186 bp AvaFXbaI fragment was ligated into pUG19 previously digested with AvaI and XbaI. The ligation reaction was transformed into *E. coli* DH5α. Ampicillin resistant transformants were screened and the correct construct (pAX1) was identified.

A second DNA fragment 1B was synthesized by PCR using oligonucleotides #3 and #4 (FIG. 7) as primers and plasmid pCB11C containing a fusion of the promoter and pre-region of the 53926 protease gene with the pro and mature regions of the BLAP gene. The fusion was made at a ClaI site and it is referred to as the Cla fusion. It was designed to include a new XbaI site at its 5' end and a new PstI site at its 3' end (FIG. 7). After restriction with XbaI and PstI the 404 bp DNA fragment was ligated into pAX1 which had previously been restricted with XbaI and PstI. The ligation reaction was transformed into *E. coli* DH5α. Ampicillin resistant transformants were screened and the correct construct (pAP1) was identified. Plasmid pAPI is comprised by the altered 53926 stem-loop region (P1) as shown in FIG. 2 followed by the DNA sequence of the 53926-BLAP ClaI fusion gene upstream of the NcoI site. A comparison of the predicted secondary structure for P1 and the wild type sequence is shown in FIG. 23.

Figure 10:
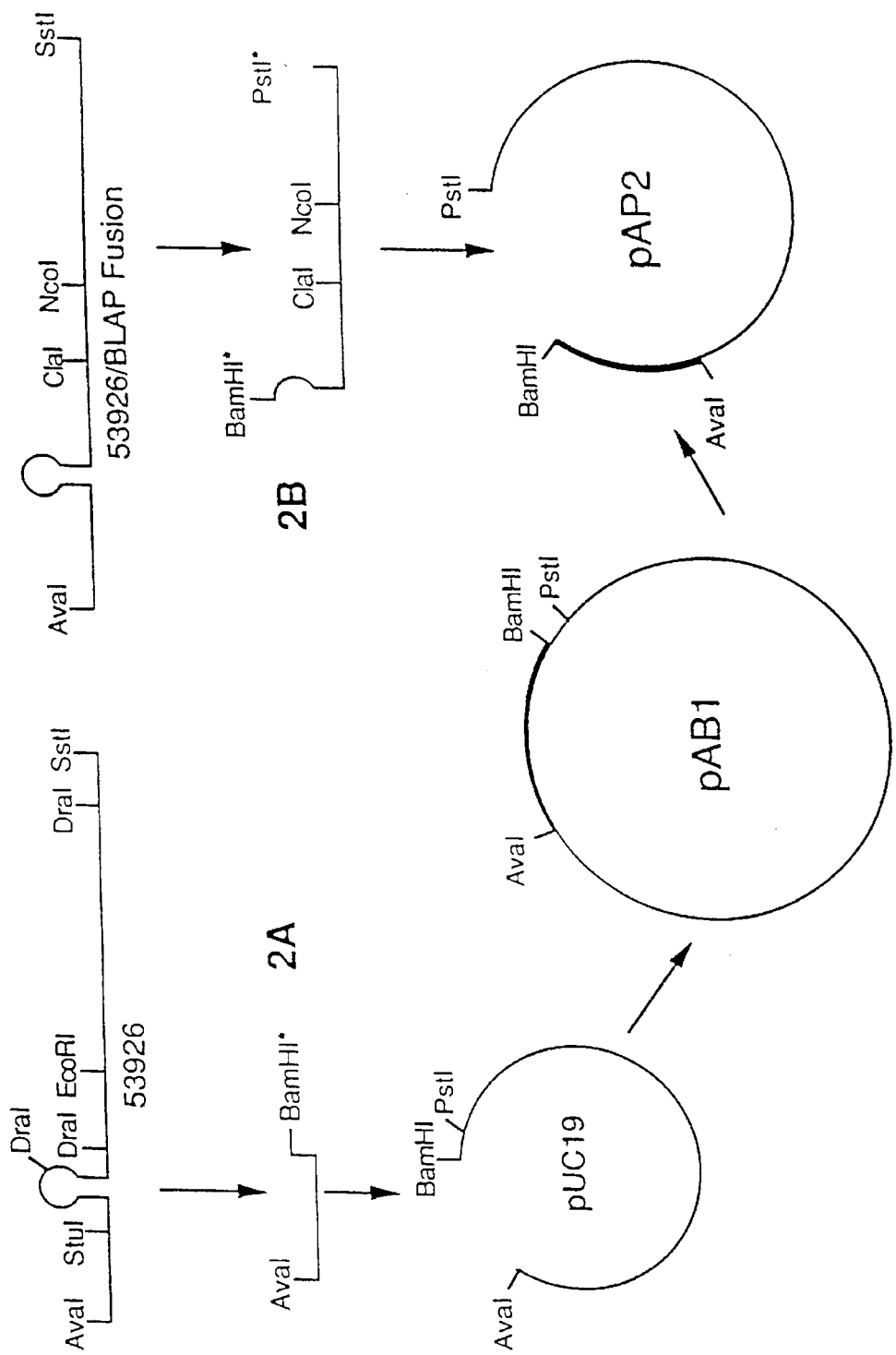
FIG. 10. Strategy for the construction of the modified P2 controlling element. The PCR fragments are designated 2A and 2B. Plasmid pAP2 contains the ATCC 53926:BLAP fusion gene from the AvaI site past the NcoI site in the coding region for mature BLAP. The two BamHI sites and the PstI site were created for cloning purposes during the PCR synthesis of fragments 2A and 2B. A detailed description of 2A and 2B is given in the text.

Plasmid pAP2 was constructed by ligating PCR fragments 2A and 2B into pUC19. A construction scheme is shown in FIG. 10. DNA fragment 2A was synthesized by PCR using oligonucleotides #1 and #5 (FIG. 6) as primers and plasmid pC50 as template. It was designed to contain an AvaI site at its 5' end and a BamHI site at its 3' end. Oligonucleotide #1 has previously been described (construct 1A), while oligonucleotide #5 introduced a new BamHI site within the stem-loop region of the 53926 sequence. After restriction of 2A with AvaI and BamHI the 166 bp AvaI/BamHI DNA fragment was ligated into pUC19 digested with the same enzymes. The ligation reaction was transformed into *E. coli* DH5α. Ampicillin resistant transformants were screened and the correct construct (pAB1) was identified. A second DNA fragment 2B was synthesized by PCR reaction using oligonucleotides #6 and #4 (FIG. 7) as primers and plasmid pCB11C as template. It was designed to include a new BamHI site at its 5' end and a new PstI site at its 3' end as already been described for DNA fragment 1B. After restriction with BamHI and PstI, the 408 bp DNA fragment 2B was ligated into pAB1 and the ligation mix was transformed into *E. coli* DH5α. Ampicillin resistant transformants were screened and the correct construct (pAP2) was identified. Plasmid pAP2 is comprised by an altered 53926 stem-loop region (P2) as shown in FIG. 2 followed by the DNA sequence of the 53926-BLAP Cla fusion gene upstream of the NcoI site. A comparison of the predicted secondary structure for P2 and the wild type sequence is shown in FIG. 23.

Figure 11:
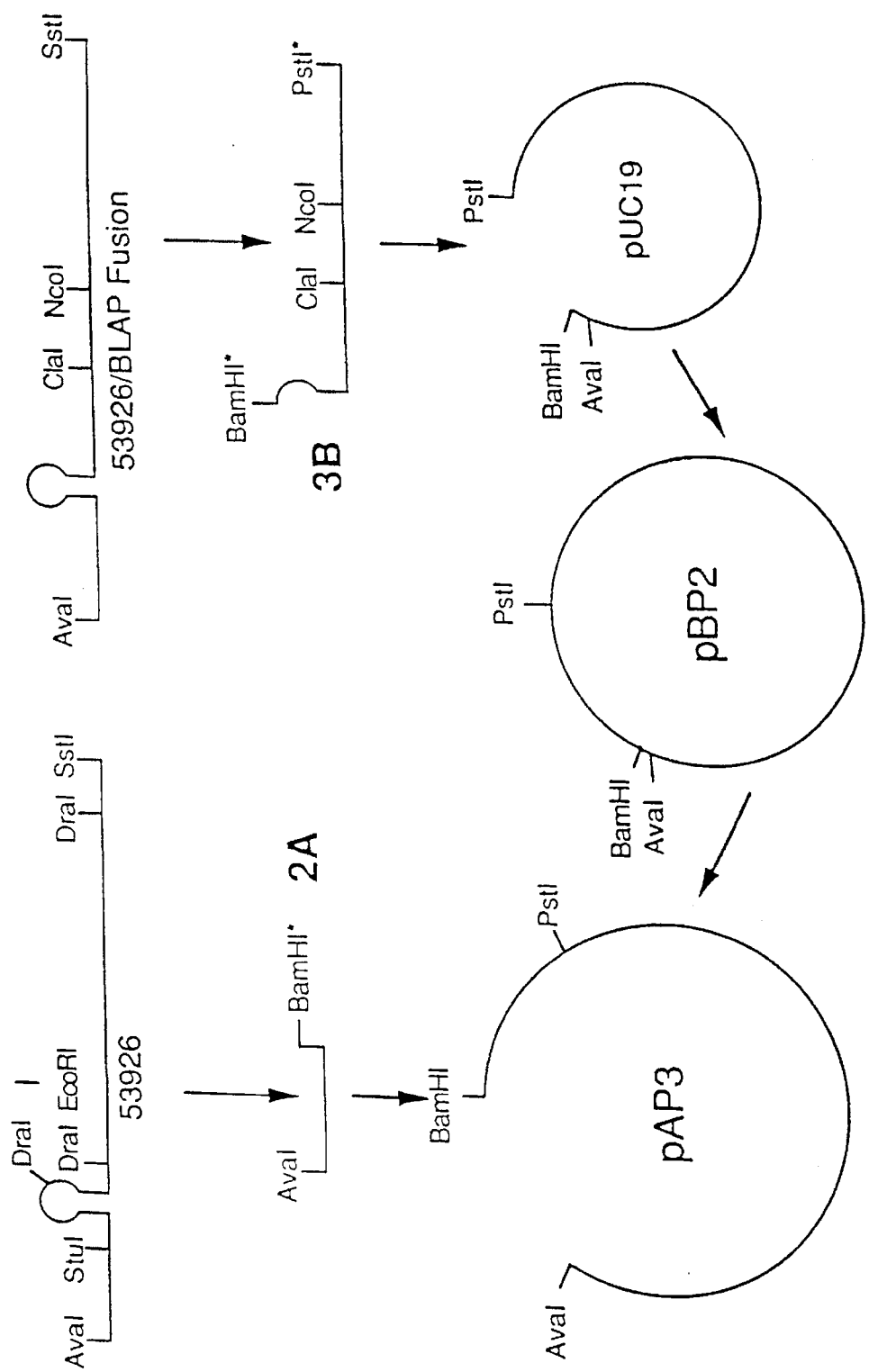
FIG. 11. Strategy for the construction of the modified P3 controlling element. The PCR fragments are designated 2A and 3B. Plasmid pAP3 contains the ATCC 53926:BLAP fusion gene from the AvaI site past the NcoI site in the coding region for mature BLAP. The two BamHI sites and the PstI site were created for cloning purposes during the PCR synthesis of fragments 2A and 3B. A detailed description of 2A and 3B is given in the text.

Plasmid pAP3 was constructed by ligating PCR fragments 2A and 3B into pUC 19. A construction scheme is shown in FIG. 11. The DNA fragment 3B was synthesized by PCR with oligonucleotides #7 and #4 (FIG. 7) as primers and plasmid pCB11C as template. It was designed to contain a new BamHI site at its 5' end and an a new PstI site at its 3' end as already described for DNA fragment 1B. After restriction with BamHI and PstI, the 430 bp DNA fragment 3B was ligated into pUC19 cut with BamHI and PstI and the ligation mix was transformed into *E. coli* DH5α. Ampicillin resistant transformants were screened and the correct construct (pBP2) was identified. Plasmid pBP2 was restricted with AvaI and BamHI and the previously described 166 bp AvaI/BamHI DNA fragment 2A was ligated in and the ligation mix was transformed into *E. coli* DH5α. Ampicillin resistant transformants were screened and the correct construct (pAP3) was identified. Plasmid pAP3 is comprised by an altered 53926 stem-loop region (P3) as shown in FIG. 2 followed by the DNA sequence of the 53926-BLAP Cla fusion gene upstream of the NcoI site. A comparison of the predicted secondary structure for P3 and the wild type sequence is shown in FIG. 23.

Figure 12:
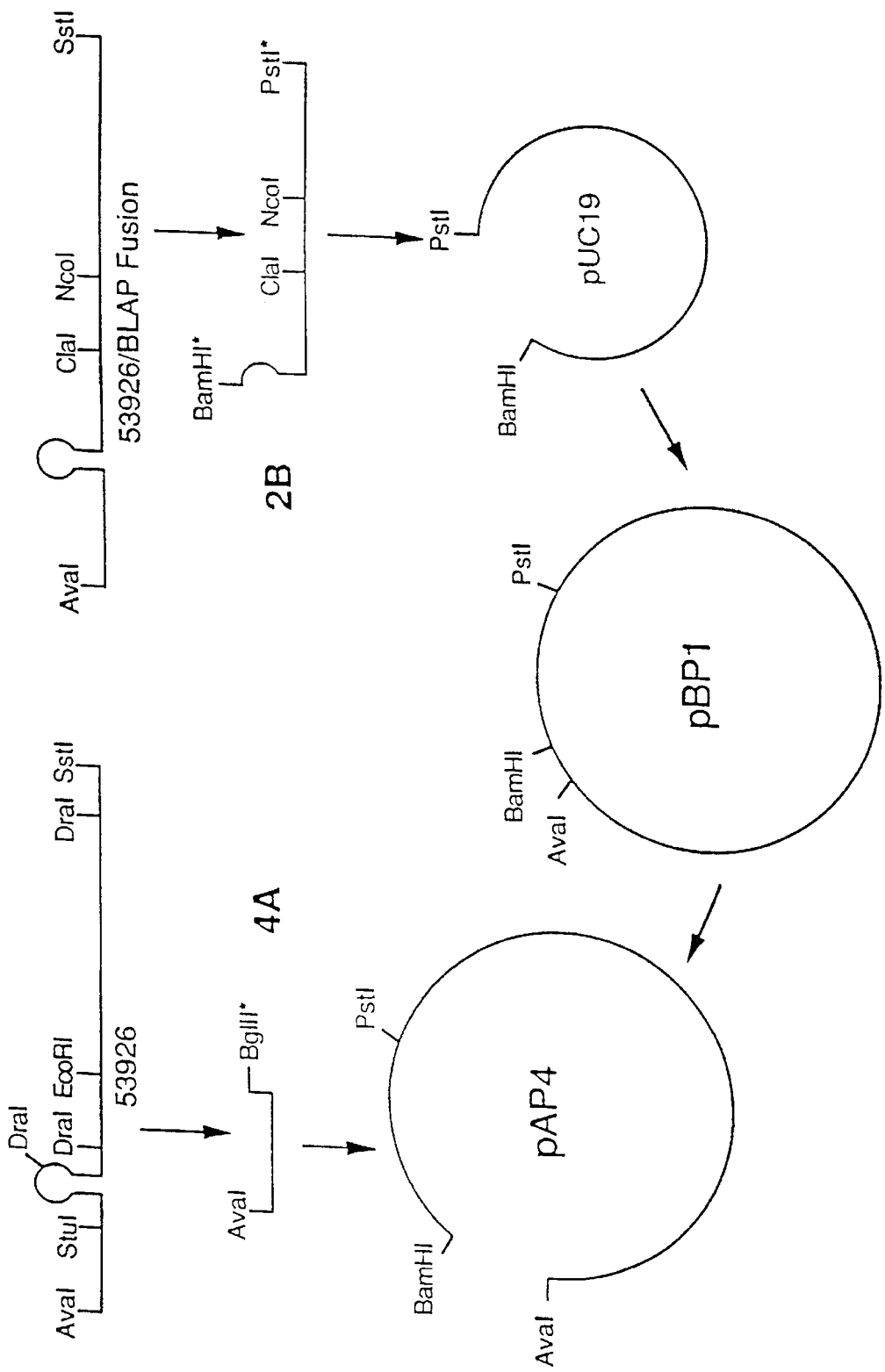
FIG. 12. Strategy for the construction of the modified P4 controlling element. The PCR fragments are designated 4A and 2B. Plasmid pAP4 contains the ATCC 53926:BLAP fusion gene from the AvaI site past the NcoI site in the coding region for mature BLAP. The BamHI, BglII and the PstI sites were created for cloning purposes during the PCR synthesis of fragments 4A and 2B. A detailed description of 4A and 2B is given in the text.

Plasmid pAP4 was constructed by ligating DNA fragments 2B and 4A into plasmid pUC19. A construction scheme is shown in FIG. 12. DNA fragment 2B (described in construct pAP2) was ligated to pUC19 cut with BamHI and PstI. The ligation mix was transformed into *E. coli* DH5α. Ampicillin resistant transformants were screened and the correct construct identified (pBP1). The DNA fragment 4A was synthesized by PCR using oligonucleotides #1 and #8 (FIG. 6) as primers and plasmid pC50 as template. It was designed to contain an AvaI site at its 5' end as described for 1A and a new BglII site at its 3' end (FIG. 6). After restriction with AvaI and BglII, the 157 bp DNA fragment 4A was ligated to pBP1 cut with AvaI and BamHI. The ligation mix was transformed into *E. coli* DH5α. Ampicillin resistant transformants were screened and the correct construct (pAP4) identified. Plasmid pAP4 is comprised by an altered 53926 stem-loop region (P4) as shown in FIG. 2 followed by the DNA sequence of the 53926-BLAP Cla fusion gene upstream of the NcoI site. A comparison of the predicted secondary structure for P4 and the wild type sequence is shown in FIG. 23.

Figure 13:
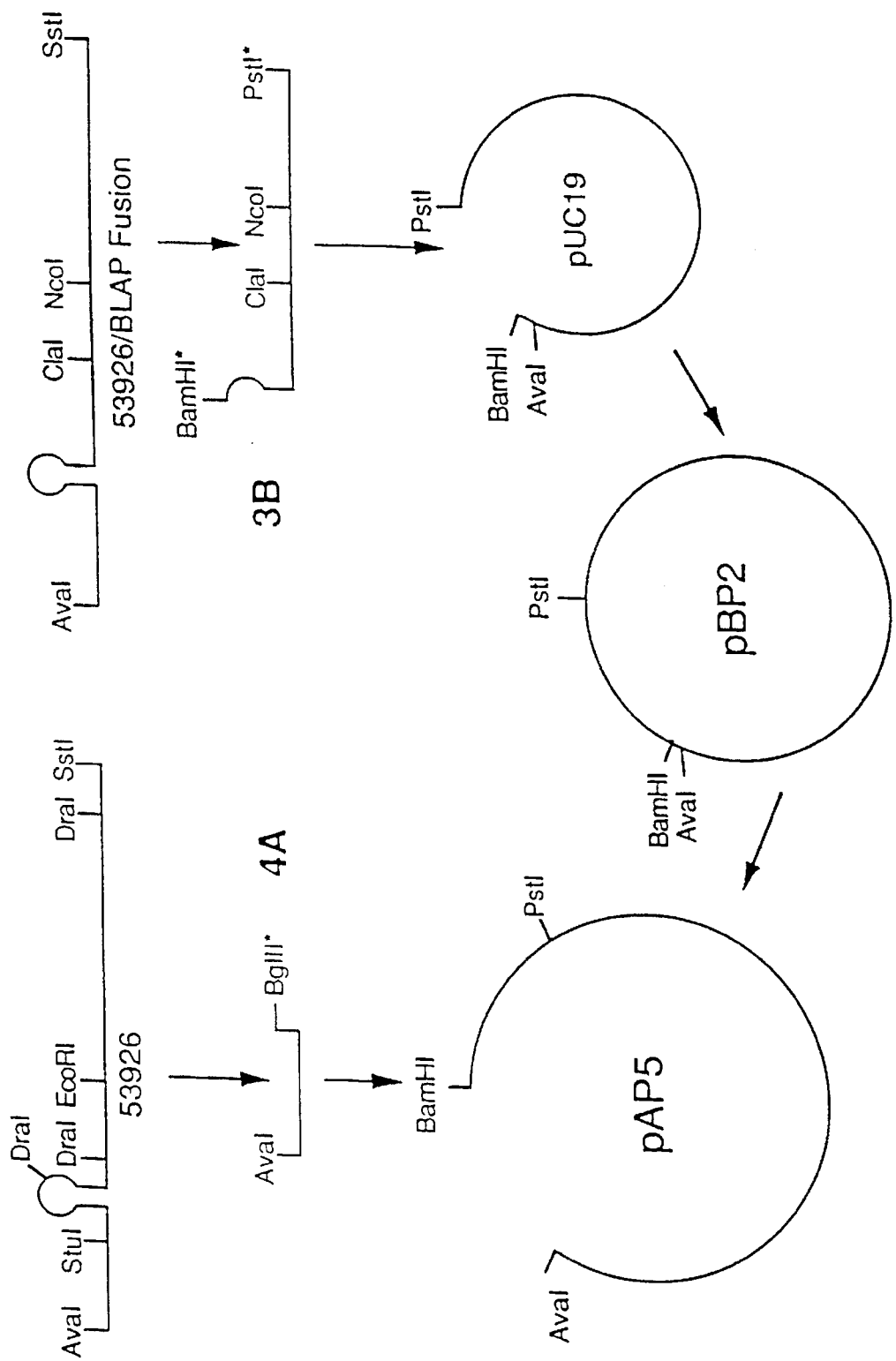
FIG. 13. Strategy for the construction of the modified P5 controlling element. The PCR fragments are designated 4A and 3B. Plasmid pAP5 contains the ATCC 53926:BLAP fusion gene from the AvaI site past the NcoI site in the coding region for mature BLAP. The BamHI, BglII and the PstI sites were created for cloning purposes during the PCR synthesis of fragments 4A and 3B. A detailed description of 4A and 3B is given in the text.

Plasmid pAP5 was constructed by ligating PCR fragment 4A into plasmid pBP2. A construction scheme is shown in FIG. 13. Plasmid pBP2 has been described (see construct pAP3). It was restricted with AvaI and BamHI and ligated to the 157 bp DNA fragment 4A. DNA fragment 4A has already been described (see construct pAP4). The ligation mix was transformed into *E. coli* DH5α and screened for Ampicillin resistant transformants. The correct construct (pAP5) was identified. Plasmid pAP5 is comprised by an altered 53926 stem-loop region (P5) as shown in FIG. 2 followed by the DNA sequence of the 53926-BLAP Cla fusion gene upstream of the NcoI site. A comparison of the predicted secondary structure for P5 and the wild type sequence is shown in FIG. 23.

EXAMPLE 6

Reconstruction of the 53926:BLAP Fusion Gene With Altered Stem-Loop Structure in *E. coli*

Figure 4:
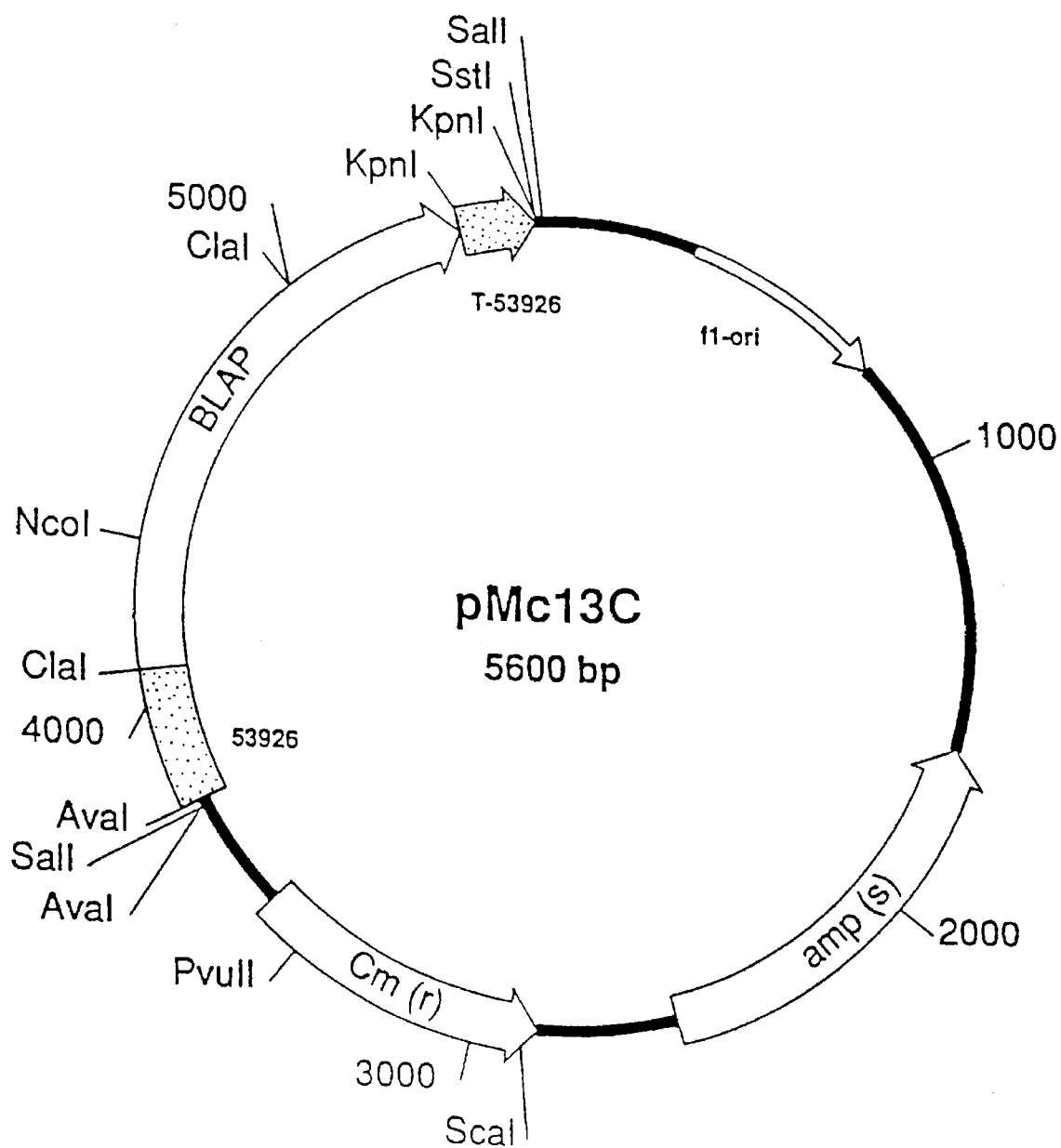
FIG. 4. Shows a restriction map of plasmid pMc13C which is a chloramphenicol resistance derivative of plasmid pMc5-8 that contains the 53926:BLAP Cla fusion gene followed by a 164 bp KpnI fragment which includes the 53926 transcription terminator sequence.
Figure 14:
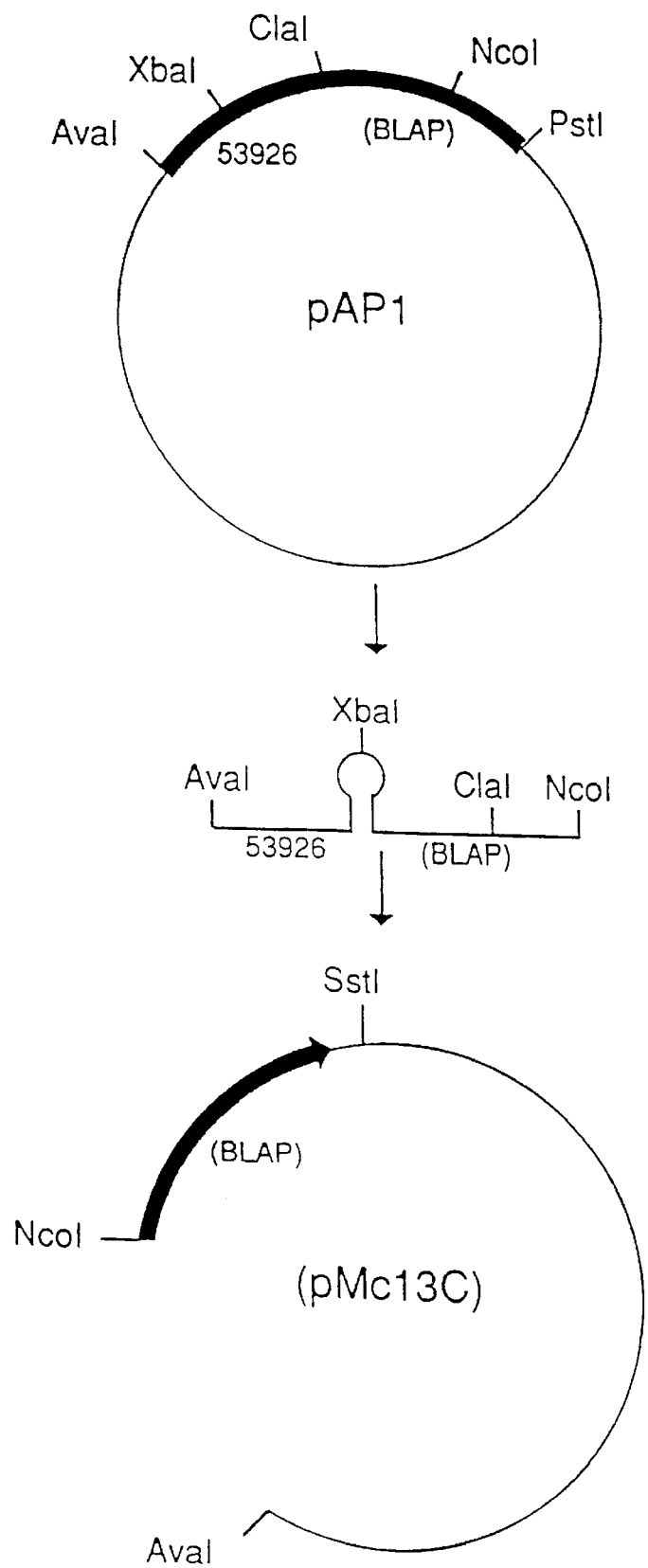
FIG. 14. Strategy for reconstituting the complete ATCC 53926:BLAP fusion gene followed by the 53926 transcription terminator. Plasmid pMc13C is described above and can be seen in detail in FIG. 4. An AvaI/NcoI fragment carrying a modified stem-loop region from plasmids pAP1, pAP2, pAP3, pAP4 and pAP5 is cloned into pMc13C which has been restricted with the same enzymes to remove the fragment carrying the wild type stem loop region. Each of the modified 53926:BLAP fusion genes was then removed on an AvaI/SstI fragment and ligated to the AvaI/SstI vector fragment from plasmids pC51 and pH70 before cloning into B. subtilis DB104.

In order to reconstruct the complete 53926:BLAP Cla fusion gene, the plasmids pAP1–pAP5 were cut with AvaI and NcoI and the small AvaI/NcoI DNA fragments containing the altered 53926 stem-loop promoters P1–P5 were then ligated to the large AvaI/NcoI fragment of plasmid pMc13C as depicted in FIG. 14 for pAP1. Plasmid pMc13C is a derivative of the plasmid pMc containing the 53926:BLAP Cla fusion gene and 53926 transcription terminator and a chloramphenicol resistance gene (FIG. 4). After restriction of pMc13C with AvaI and NcoI, the large DNA fragment, containing the vector sequences and the promature region of the 53926:BLAP fusion gene, was isolated from an agarose gel either by electroelution or by HPLC purification. The purified fragment was ligated to the AvaI/NcoI digested pAP derivatives. The ligation mix was transformed into *E. coli* DH5α. Several chloramphenicol resistant transformants were analyzed by restriction analysis. The correct constructs, which contain the P1–P5 promoter regions with the 53926:BLAP fusion gene and the 53926 transcription terminator sequence were named pMc13P1, pMc13P2, pMc13P3, pMc13P4, and pMc13P5.

All constructs were verified by DNA sequencing of the promoter region which includes the stem-loop structure (data not shown). The DNA sequencing revealed that an unwanted point mutation had occurred in mutant P1 within the ribosomal binding site where an Adenine had been altered to a Thymine (TAAAG ... to TAtAG) (FIG. 2). This point mutation is present in all constructs with the P1 promoter.

CsCl gradient purified DNA of all five pMc13P constructs was prepared and digested with AvaI and SstI. The AvaI/SstI fragments containing the altered 53926:BLAP Cla fusion genes were used for the subcloning into Bacillus vectors.

EXAMPLE 7

Subcloning of the 53926:BLAP Fusion Genes With Altered Stem-Loops into B. subtilis DB104

The 53926:BLAP fusion genes with the altered stem-loop regions were subcloned into derivatives of Bacillus vectors pBC16 and pUB110 called pC51 (FIG. 15) and pH70 (FIG. 16), respectively. The large AvaI/SstI vector DNA fragments of pC51 and pH70 were purified and ligated with the AvaI/SstI digested E. coli vectors containing the 53926:BLAP mutant genes in a molar ration of 1:2 and transformed into physiological competent cells of B. subtilis DB 104. Control ligations of the isolated AvaI/SstI fragment of pC51 or pH70 did not show any transformants. Most transformants made clearing zones on skim milk plates showing that an active protease was expressed and secreted. Plasmid DNA was prepared from several transformants which made clearing zones using Qiagen columns according to the manufacturers instructions (QIAGEN Inc., Chatsworth, Calif.). The correctness of each construct was verified by restriction analysis and by determining the DNA sequence across the 53926 promoter region (data not shown).

The promoter mutants P1–P5 cloned into pC51 were called: pCB56C-P1, pCB56C-P2, pCB56C-P3, pCB56C-P4 and pCB56C-P5, because these plasmids have the same composition as pCB56C with the exception of the altered stem-loop region.

The promoter mutants P1–P5 cloned into pH70 were called: pCB76C-P1, pCB76C-P2, pCB76C-P3, pCB76C-P4 and pCB76C-P5, because these plasmids have the same composition as plasmid pCB76C with the exception of the altered stem-loop region.

Plasmid constructs mimicking pCB75C were constructed by deleting the 53926 transcription terminator contained on the 164 bp KpnI fragment from the pCB76C-P1–P5 constructs. pCB76C-P1–P5 Plasmid DNA's were purified from the B. subtilis DB104 transformants, restricted with KpnI, religated and transformed back into B. subtilis DB 104. Transformants with the correct constructs DNAs were identified by restriction analysis. These plasmids were designated pCB75C-P1, pCB75C-P2, pCB75C-P3, pCB75C-P4 and pCB75C-P5.

EXAMPLE 8

Cloning the pCB56C-P1 Through P5 Plasmids into B. licheniformis ATCC 53926

Plasmid DNA's were purified from B. subtilis DB104 and continued to be correct by restriction analysis and DNA sequencing across the stem-loop region. The same DNA's were used to transform B. licheniformis ATCC 53926 using the protoplast technique as described by Chang, C., and Cohen, S. N.,(1979) Mol. Gen. Genet. 168, 111–115.

EXAMPLE 9

Shake Flask Cultivation and Sampling

For B. subtilis 10 flasks were used for the wild type control strain and 7 flasks for each mutant. For B. licheniformis 11 flasks were used for the control strain and 7 flasks for each mutant. Precultures from a fresh streak plate were inoculated into 50 ml of luria broth (LB) containing either kanamycin at 20 µg/ml or 15 µg/ml tetracycline and allowed to grow at 37° C., 240 rpm for approximately 6 hours. A 5% transfer (5 ml per 100 ml shake flask media) from the precultures was then used to inoculate Erlenmeyer flasks (500 ml, Bellco with metal caps) containing 100 mls of MLBSP medium (refer to Table 1 for composition). After addition of the preculture, shake flasks were incubated at 37° C., 240 rpm for a total of from 68 to 72 hours, with three 1.5 ml samples taken at approximately 12 hour intervals to determine cell counts, optical density, pH and protease content. Growth was monitored by measuring Absorbance at 600 nm ($A_{600}$) of broth samples diluted in deionized $H_2O$ and by determining cell counts by plating dilutions of each strain on duplicate luria agar plates containing 1% skim milk and the appropriate antibiotic. pH values were determined by direct measurement of 1.5 ml of shake flask culture. Protease activity was measured using either the HPE or the AAPF assays (described below) on sample broth supernatant after centrifugation (10,000×g) at room temperature for 15 minutes.

TABLE 1

Composition of MLBSP Medium

| Component | Quantity (for 1 liter of media) |
| --- | --- |
| deionized water | 750 ml |
| Difco Casitone | 10 gm |
| Difco Tryptone | 20 gm |
| Difco Yeast Extract | 10 gm |
| NaCl | 5 gm |
| Na—Succinate | 27 gm |

Adjust media to pH 7.2 by addition of NaOH, and the volume to 815 ml with water. Autoclave at 121° C., 15 psi for 15 min.
Cool media before addition of the following sterile stock solutions:

| Component | | Quantity (for 1 liter of media) |
| --- | --- | --- |
| $MgSO_4.7H_2O$ | (100 mg/ml stock, autoclaved) | 1 ml |
| $CaCl_2.2H_2O$ | (30 mg/ml stock, autoclaved) | 2.5 ml |
| $MnCl_2.2H_2O$ | (1 mM stock, autoclaved) | 0.5 ml |
| $FeSO_4.7H_2O$ | (1 mM stock, filter sterilized) | 0.5 ml |
| Glucose | (25% (w/v) stock, autoclaved) | 80 ml |
| PIPES Buffer[1] | (pH 7.2, 1M stock, autoclaved) | 50 ml |
| $KPO_4$ Buffer[2] | (pH 7.0, 1.5M stock, autoclaved) | 50 ml |

[1]Piperazine—N,N'bis(2-ethane sulfonic acid).
[2]A sufficient amount of 1.5M dibasic phosphate ($K_2HPO_4$) was added to 200 ml of 1.5M monobasic phosphate ($KH_2PO_4$) to adjust pH to 6.0. The final pH was adjusted to 7.0 with 4M KOH.
Either kanamycin or tetracycline antibiotic stock solutions were added to the media just before use to a final concentration of 20 µg/ml and 15 µg/ml respectively.

EXAMPLE 10

Promoter Shake Flask Study in B. subtilis (Protease Measurements)

Figure 17:
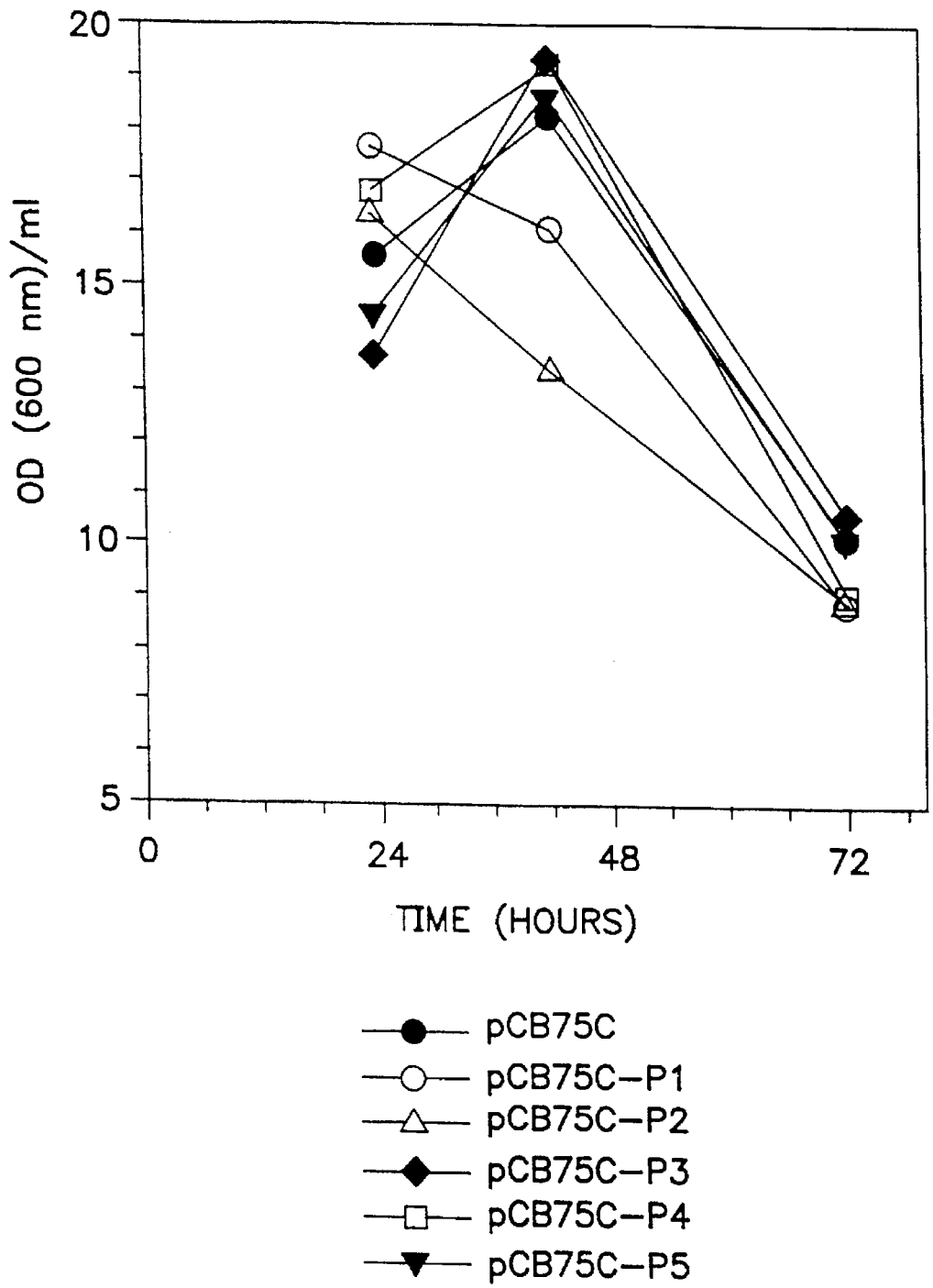
FIG. 17. Absorbance ($OD_{600}$) readings for the B. subtilis DB104 cultures carrying the P1–P5 controlling elements cloned into derivatives of plasmid pCB75C. The values shown are averages of 10 flasks for the pCB75C control strain and 7 flasks for each of the stem-loop mutants.
Figure 20:
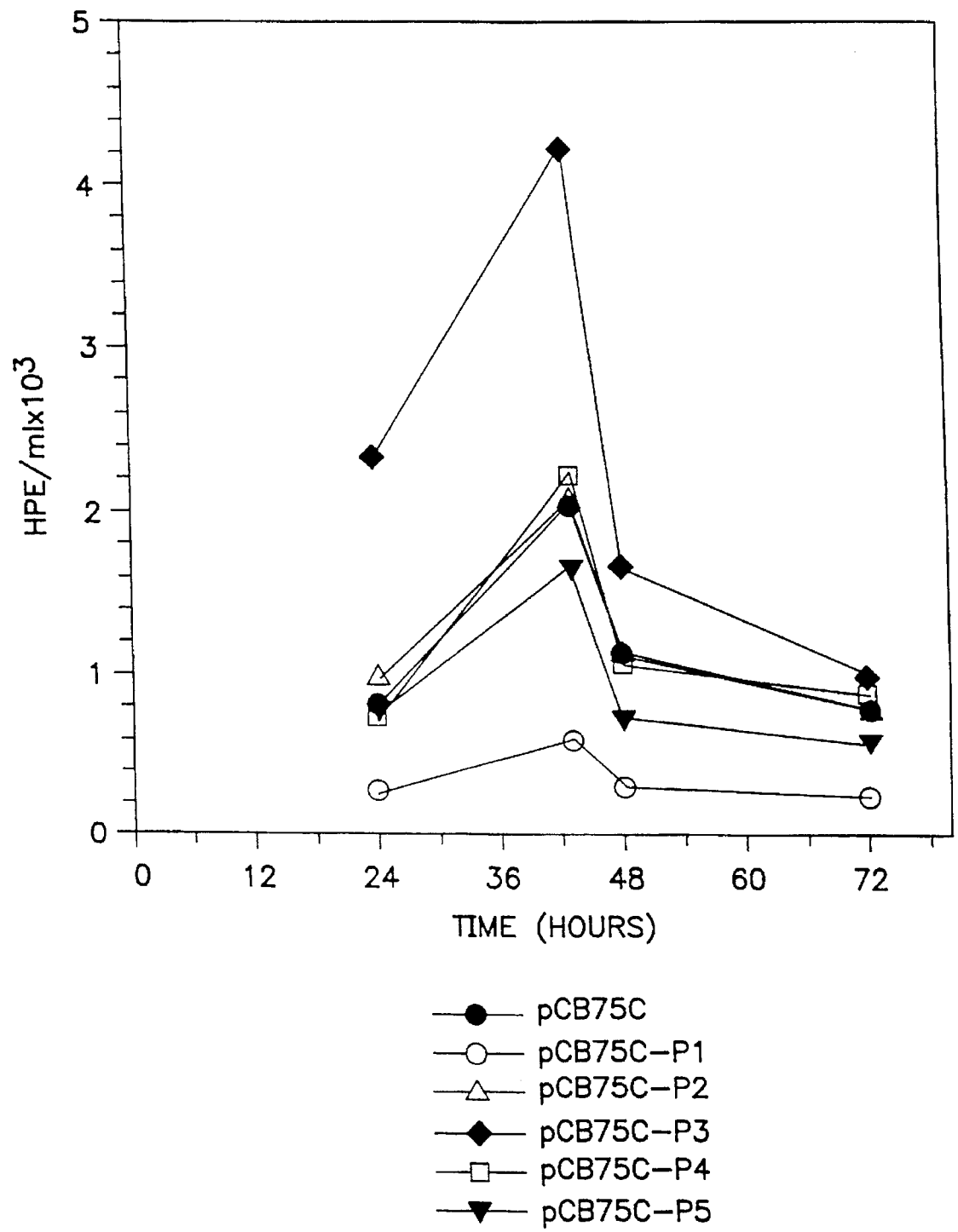
FIG. 20. Protease production in shake flasks of B. subtilis DB104 transformed with pCB75C (control strain) and the P1–P5 derivatives of pCB75C. Protease values were calculated by the HPE method described in Example 3. Each point on the graph represents the average of either 7 flasks for each strain carrying a P construct or 10 flasks for the pCB75C control strain.

The pCB75C type constructs were used to analyze protease yields because this construct had proven the most productive with regard to BLAP production in *B. subtilis*. The protease production of *B. subtilis* DB104 strains transformed with derivatives of plasmid pCB75C carrying the 53926:BLAP fusion gene with the wild type stem-loop structure and the various stem-loop routants was monitored by taking samples at 24, 43, 48, and 72 hours. The results of the HPE assays and the calculated z values are listed in Table 2. An analysis of the protease production using the z test revealed a significant increase in the protease produced by mutant P3 in pCB75C are as compared to the control group (pCB75C, with no mutations in the promoter region). Mutants P1 and P5 showed significant decreases in protease activity as compared to the pCB75C control. A graphic plot of the data contained in Table 2 can be seen in FIG. 20. As can be seen in this graph, P3 has increased protease production as compared to the pCB75C control, whereas the P1 and P5 constructs are characterized by decreased protease production. Constructs P2 and P4 had approximately the same protease production as the pCB75C control. The optical density measurements and (FIG. 17) confirmed that differences in protease activity were not the result of differences in cell growth. While all of the cultures demonstrated good growth, construct P3, which had significantly higher protease activity, had the lowest OD reading at both the 48 hr and 72 hr sample times.

All constructs were expected to produce the BLAP protease and this was confirmed by tryptic digest map analysis (FIG. 8) of proteases purified by ion exchange chromatography. When the protease produced by P1–P5 were mixed with BLAP no shifts or new peptides were observed, indicating that the promoter mutant proteins are indeed BLAP. The purified proteins were also analyzed by gel electrophoresis using the Pharmacia PhastGel system with Reverse Polarity for basic proteins which is a native gel electrophoresis system. All of the proteins migrated identically to the Blap control.

TABLE 2

DB104 Promoter Shake Flask Study pCB75C derivatives
AAPF Assay (U/ml)

| Sample | 24 hours | 43 hours | 48 hours | 72 hours |
|---|---|---|---|---|
| pCB75C Control average | 840 | 2090 | 1190 | 890 |
| pCB75C-P1 average | 310 | 660 | 370 | 360 |
| z test value | 3.2 | 8.8 | 8.1 | 20.1 |
| pCB75C-P2 average | 1020 | 2150 | 1190 | 900 |
| z test value | 1.1 | 0.37 | 0 | 0.36 |
| pCB75C-P3 average | 2360 | 4270 | 1720 | 1100 |
| z test value | 9.2 | 13.4 | 5.3 | 7.95 |
| pCB75C-P4 average | 780 | 2280 | 1130 | 990 |
| z test value | 0.36 | 1.17 | 0.56 | 3.80 |
| pCB75C-P5 average | 830 | 1720 | 810 | 720 |
| z test value | 0.06 | 2.28 | 3.73 | 6.44 |

The control values are an average of eleven shake flasks. pCB75P1–pCB75P5 values are an average of seven shake flasks.

EXAMPLE 11

Promoter Shake Flask Study in *B. Licheniformis* (Protease Measurements)

Figure 21:
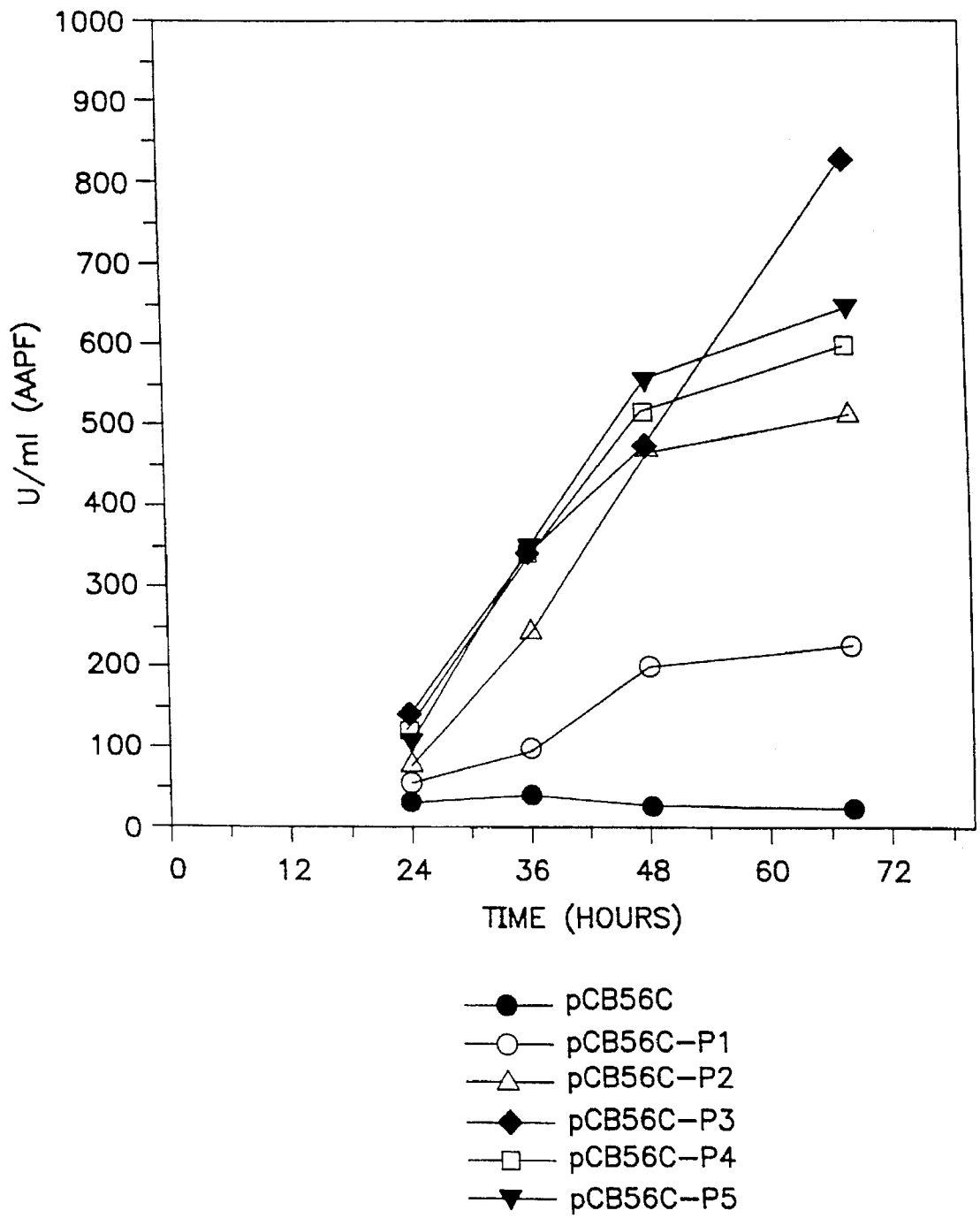
FIG. 21. Protease production in shake flasks of B. licheniformis ATCC 53926 transformed with pCB56C (control strain) and the P1–P5 derivatives of pCB56C. Protease values were calculated by the AAPF method described in Example 3. Each point on the graph represents the average of either 7 flasks for each strain carrying a P construct or 11 flasks for the pCB56C control strain.

Previous results had shown that plasmid pCB56C was superior to pCB75C or pCB76C for protease production in *B. licheniformis* ATCC 53926. Therefore, the pCB56C-P1–P5 constructs were chosen to evaluate the effects of the stem-loop alterations on protease production in *B. licheniformis* ATCC 53926. The protease production of *B. licheniformis* ATCC 53926 strains transformed by derivatives of plasmid pCB56C caroling the 53926:BLAP fusion gene with the wild type stem-loop structure and the various stem-loop routants was monitored by taking samples at 24, 36, 48, and 68 hours. The results of the AAPF assays are listed in Table 3. An analysis of the protease production using the z test reveals a significant increase in the protease produced by routants P1, P2, P3, P4 and P5 in pCB56C as compared to the control group (pCB56C with no mutations in the stem-loop region). The protease activity as a function of time is shown graphically in FIG. 21. At 68 hours, promoter mutations P1, P2, P3, P4, P5 have significantly increased (>5 fold) protease production as compared to the pCB56C control. The best productivity was associated with mutant P3 which showed a 25 fold increase over the control strain, while the lowest increase was 8 fold for mutant P1. The decreased protease production of P1 as compared to P2–P5 may have been the result of the point mutation in the ribosomal binding site discussed previously.

Figure 18:
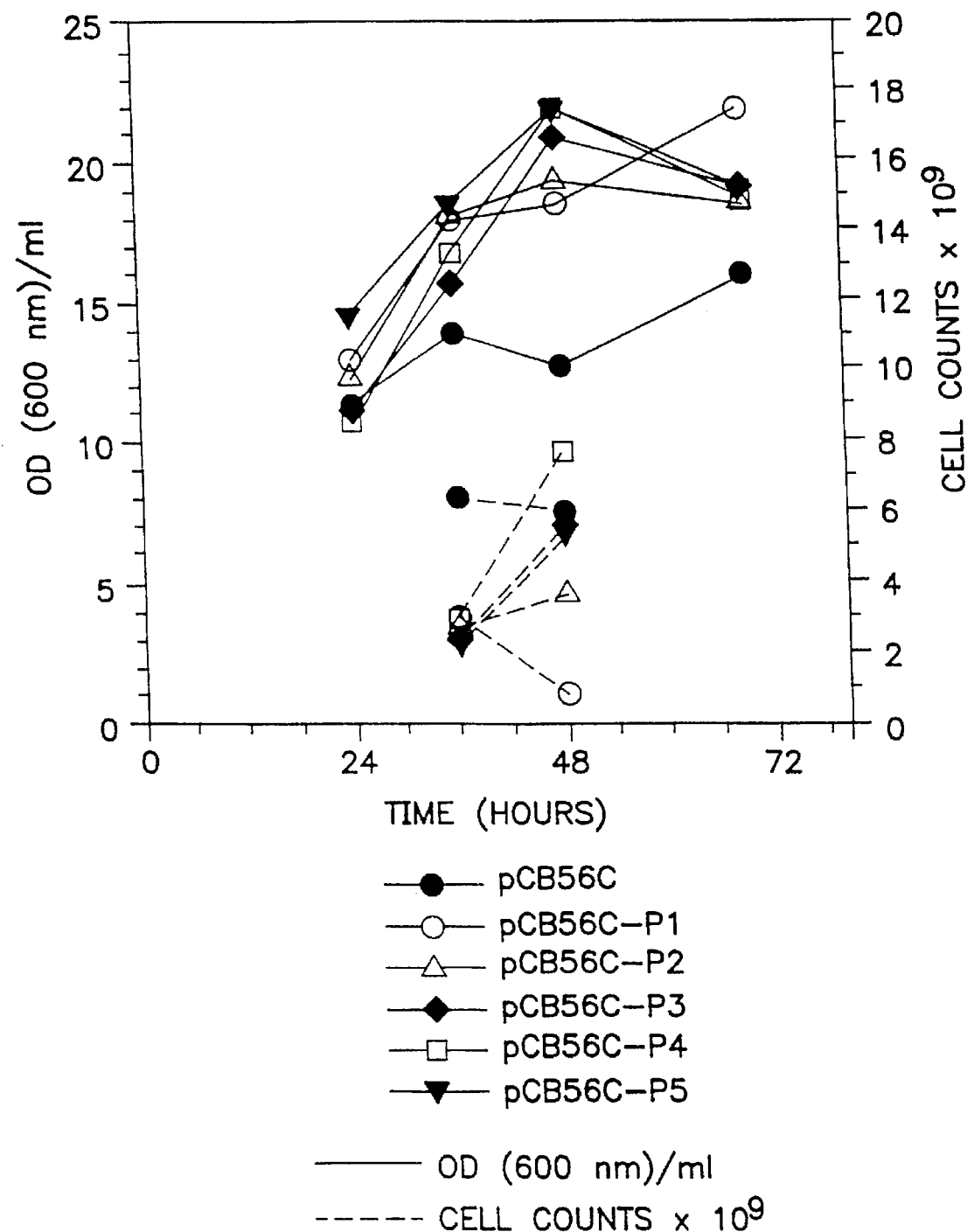
FIG. 18. Absorbance ($OD_{600}$) readings and cell count determinations for B. licheniformis ATCC 53926 cultures carrying the P1–P5 controlling elements cloned into derivatives of plasmid pCB56C. The OD values are averages of 11 flasks for the pCB56C control strain and 7 flasks for each of the stem-loop mutants. No cell counts were available for the 24 hour samples due to too many colonies on the highest dilution plated.
Figure 19:
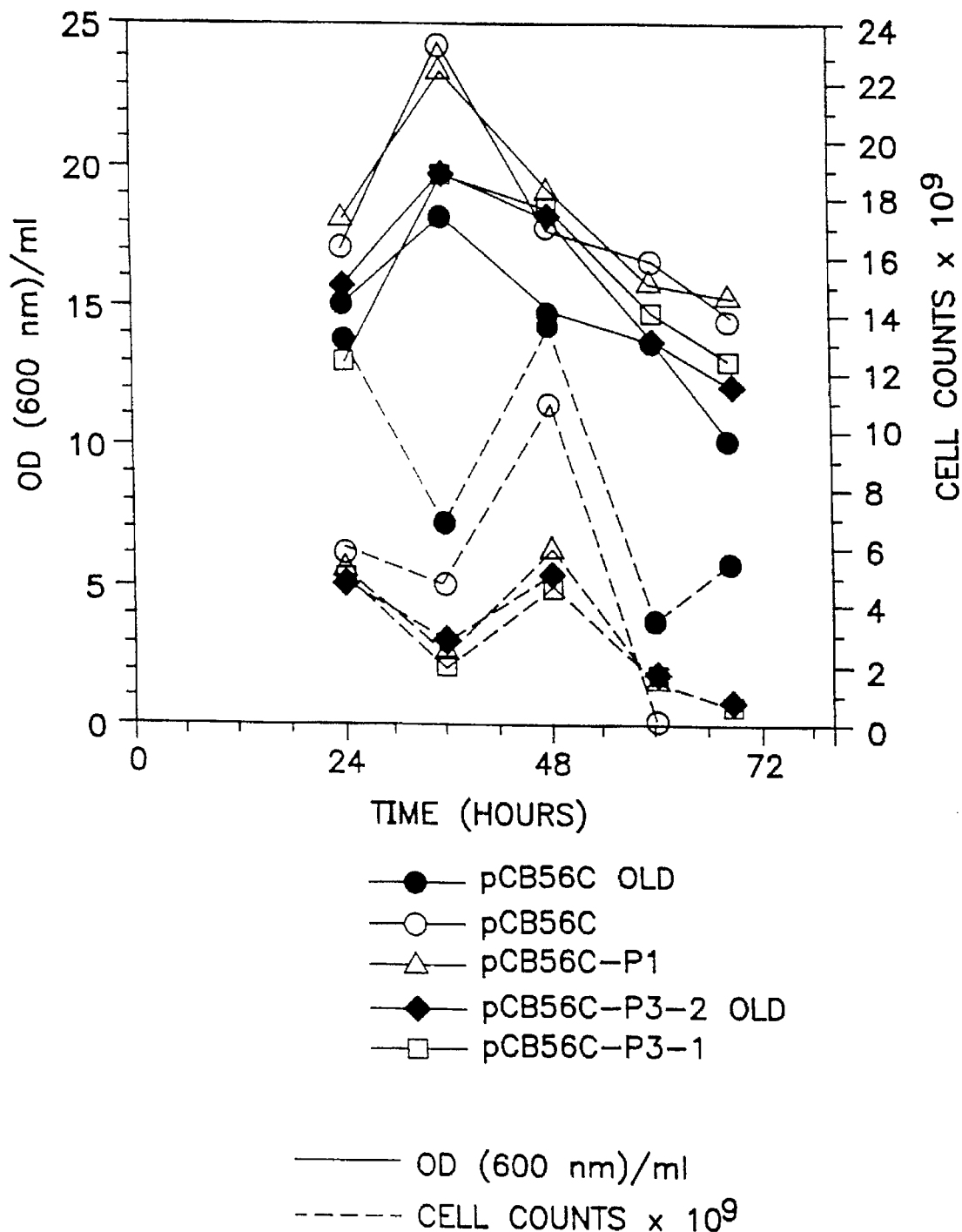
FIG. 19. Absorbance ($OD_{600}$) readings and cell count determinations for ATCC 53926 cultures carrying pCB56C, pCB56C-P1 and pCB56C-P3. B. licheniformis ATCC 53926 transformed at different times with pCB56C and pCB56C-P3 were compared to see if the observed differences in protease production were the result of strain variation. The OD values are averages of 11 flasks for the pCB56C control strain and 7 flasks for each of the stem-loop mutants. The cell counts were the average of at least two plates at the same sample dilution.

Optical density measurements and cell counts (FIG. 18) confirmed that all of the cultures exhibited growth similar to the control strain. The OD readings indicated that the control strain pCB56C did not grow as well as the other mutants, but cell counts done at 36 and 48 hours were very close to cell counts for the P1–P5 mutant strains.

TABLE 3

E312 Promoter Shake Flask Study pCB56C derivatives
AAPF Assay (U/ml)

| Sample | 24 hours | 36 hours | 48 hours | 68 hours |
|---|---|---|---|---|
| pCB56C Control average | 21 | 35 | 21 | 30 |
| pCB56C-P1 average | 47 | 96 | 200 | 234 |
| z test value | 6 | 12 | 75 | 32 |
| pCB56C-P2 average | 65 | 240 | 470 | 517 |
| z test value | 6 | 40 | 190 | 77 |
| pCB56C-P3 average | 135 | 337 | 471 | 832 |
| z test value | 26 | 58 | 190 | 127 |
| pCB56C-P4 average | 120 | 339 | 519 | 611 |
| z test value | 23 | 59 | 210 | 92 |
| pCB56C-P5 average | 98 | 339 | 553 | 652 |
| z test value | 18 | 59 | 224 | 98 |

The control values are an average of ten shake flasks. pCB56P1–pCB56P5 values are an average of six shake flasks.

EXAMPLE 12

Shake Flask Study to Determine the Effects of Strain Variation of Protease Production in *B. licheniformis*

Figure 22:
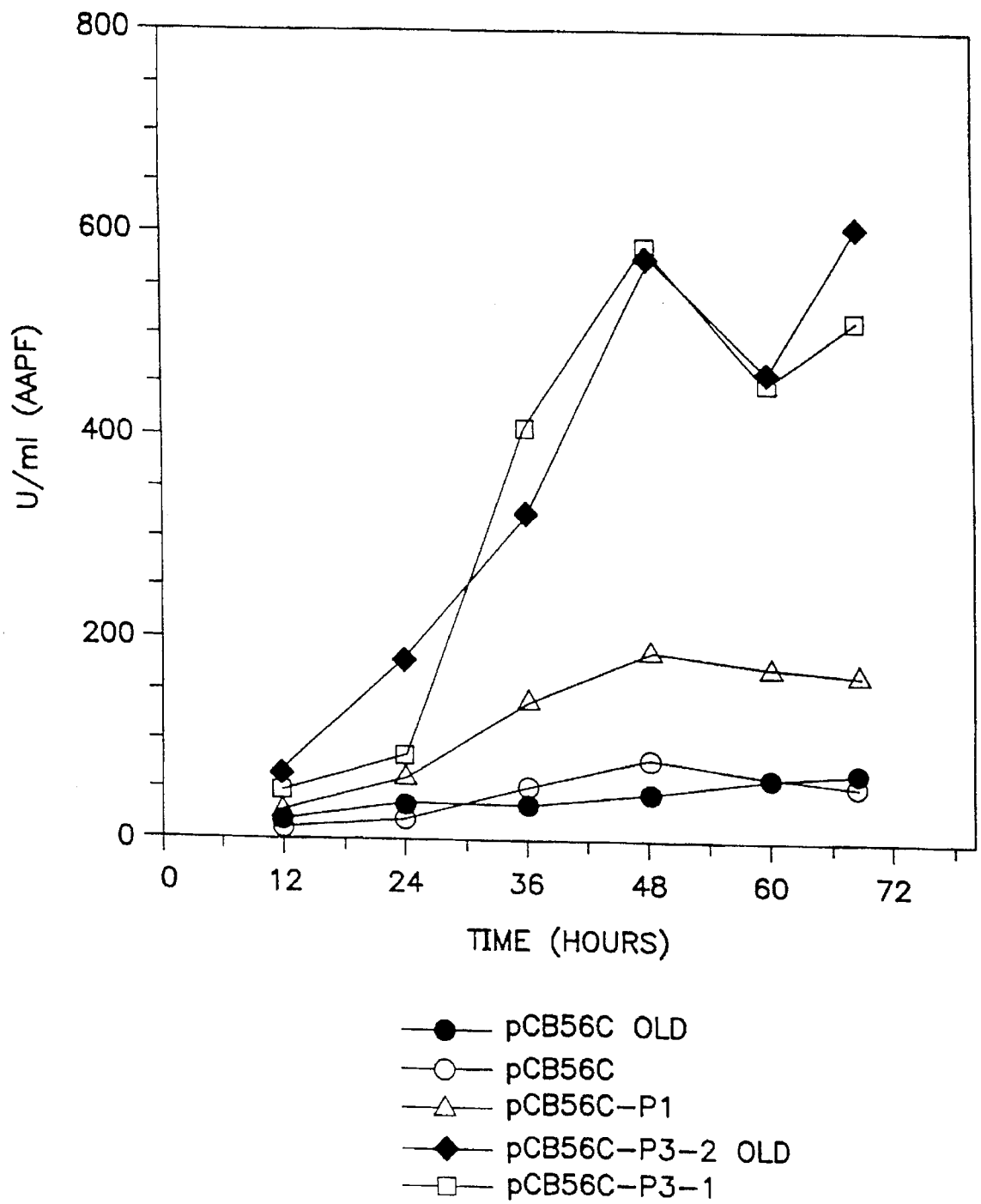
FIG. 22. Protease production in shake flasks of B. licheniformis ATCC 53926 transformed with plasmids pCB56C, pCB56C-P1 and pCB56C-P3. B. licheniformis ATCC 53926 transformed at different times with pCB56C and pCB56C-P3 were compared to see if the observed differences in protease production were the result of strain variation.

An experiment was performed to ensure that the increased protease productivity observed for pCB56C P1–P5 were not the result of *B. licheniformis* strain variation. The protease productivity of P1 and P3 in pCB56C as compared to the pCB56C control was repeated in shake flasks. This study compared control cultures of *B. licheniformis* ATCC 53926 which had been transformed with plasmid pCB56C at an early date (1988), and a later (1994) date. At the same time transformants or *B. licheniformis* transformed with pCB56C-P1 and P3 in 1988 were compared to a 1994 transformant with pCB56C-P3. The results of the AAPF (SEQ. ID NO. 9) assays are listed in Table 4. The results of this experiment, shown graphically in FIG. 22, confirm that both pCB56C-P1 and pCB56-P3 produce significantly more protease production as compared to the pCB56C control strain. At 68 hours strain pCB56-P1 had a slightly better production of protease (2.2 fold increase) as compared to the control strain, while both the old and new pCB56C-P3 transformants of *B. licheniformis* exhibited greater than a five-fold increase in protease activity. Optical density measurements and cell count determinations again confirmed that the control strains of pCB56C grew as well or better than the P1 or P3 mutant strains negating any argument that the observed differences in protease activity were the result of variations in growth. These results eliminate strain variation as a cause of the increased protease productivity associated with P2, P3, P4 and P5.

TABLE 4

E312 Promoter Shake Flask Study pCB56C derivatives AAPF Assay (U/ml)

| Sample | 12 hr. | 24 hr. | 36 hr. | 48 hr. | 60 hr. | 68 hr. |
|---|---|---|---|---|---|---|
| pCB56C old #1 | 14 | 32 | 36 | 53 | 69 | 81 |
| pCB56C #1 average | 11 | 19 | 55 | 87 | 71 | 70 |
| z value | 1.8 | 1.9 | 2.6 | 4.9 | 0.2 | 1.1 |
| pCB56C P1 average | 24 | 62 | 141 | 193 | 179 | 178 |
| z value | 5.3 | 21.1 | 8.8 | 14.4 | 16.5 | 7.8 |
| pCB56C P3-2 old average | 54 | 176 | 328 | 580 | 471 | 614 |
| z value | 24.5 | 20.8 | 39.7 | 75.9 | 42.8 | 54.4 |
| pCB56C P3-1 average | 47 | 83 | 410 | 585 | 460 | 529 |
| z value | 14.7 | 31.4 | 36.2 | 72.4 | 59.6 | 33.1 |

These values are an average of six shake flask.

EXAMPLE 13

BLAP Purification

Fermentation broth from shake flasks, on average 180 ml, was collected and clarified by centrifugation at 20,000×$g_{av.}$ for 15 min. The supernatant was placed, with stirring, on ice and after 30 min the pH of the solution was adjusted to 5.8 with glacial acetic acid. If not mentioned otherwise, all subsequent steps were performed on ice or at 4° C. The solution was clarified again by centrifugation (20,000×$g_{av.}$ for 15 min) and was concentrated approximately 4-fold by ultrafiltration (Amicon; YM30 membrane). The dark brown solution was placed in dialysis robing (Spectrapor; #1, 6 to 8 KDa molecular-weight-cut-off, 1.7 ml/cm) and dialyzed for 16 hours in 20 mM HEPES/Na$^+$, pH 7.8, containing 1 mM CaCl$_2$ ('HEPES buffer'). The dialysate was clarified by centrifugation (20,000×$g_{av.}$ for 10 min) and the pH of the solution, if necessary, was adjusted to 7.8 with 2N NaOH. The enzyme solution was loaded at a flow rate of 60 ml/hour onto a column of s-sepharose fast-flow (SSFF) (Sigma Chemical Co., St. Louis, Mo.) (15 mm diameter, 75 mm long), previously equilibrated with HEPES buffer. When all colored by-products were eluted, the column was washed with 50 ml of HEPES buffer. Then, the enzyme was eluted with 0.25M NaCl in HEPES buffer. Fractions of 1.2 ml were collected into tubes containing 0.5 ml of 100 mM MES/Na$^+$, pH 5.8. Protein content in fractions was monitored either by a UV detector set at 280 nm or by protein assay as described below. Pooled fractions containing protease protein were placed on ice and protein was precipitated with a 5 to 8-fold volume excess of acetone at −20° C. The protein was allowed to precipitate for 6 min, the mixture was centrifuged for 4 min at 6,600×$g_{av.}$, the supernatant was discarded, the pellet was briefly exposed to vacuum (water aspirator) to remove most of the acetone, and the pellet was dissolved in 20 mM MES/Na$^+$, pH 5.8, to give an approximate protein concentration of 30 mg/ml. Prior to any assays, the solution was centrifuged in an Eppendorf centrifuge for 3 min at full speed (13,000×$g_{max}$).

EXAMPLE 14

Tryptic Analysis of Proteases

Figure 8:
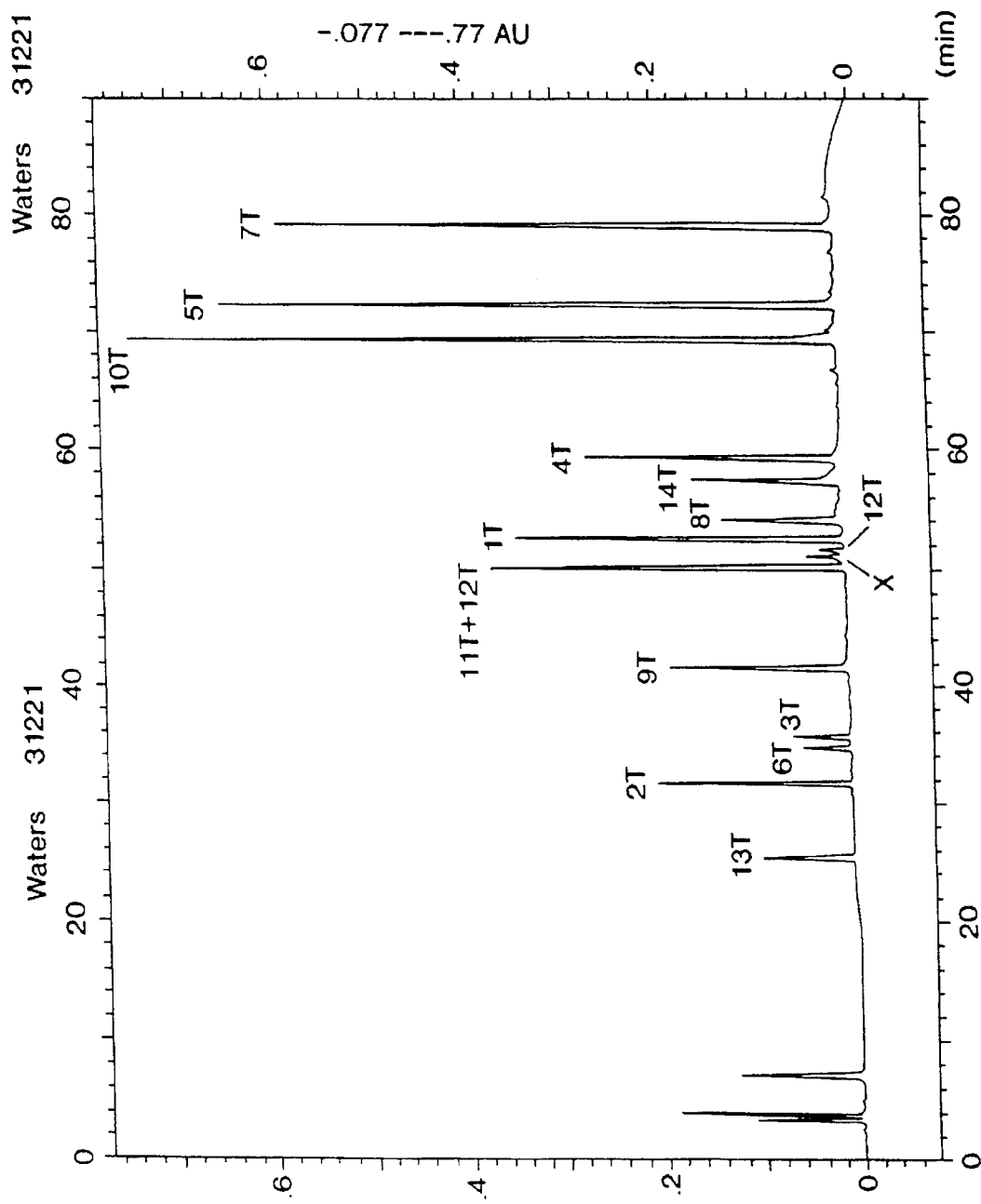
FIG. 8. Shows the HPLC peptide profile of a tryptic digest of the B. lentus alkaline protease (BLAP). The details of protease purification and treatment and HPLC conditions are described in the text. All of the proteases produced with the altered promoter elements P1–P5 gave peptide profiles indistinguishable from BLAP.

To ensure that the predominant protease activity was BLAP, purified proteases from the various promoter mutants were digested with trypsin and analyzed by HPLC for comparison of the peptide elution pattern. The number of peaks, their height and elution times were compared with results for wild type BLAP (FIG. 8).

An aliquot of up to 5 mg of protease from a stock solution was placed on ice in a 2.2-ml Eppendorf tube, then mixed with 1.0ml of 0.15N HCl and water (both chilled) to give a final concentration of 3.33 mg.ml$^{-1}$ protein and 0.1N HCl in a total volume of 1.5 ml. After the mixture had been incubated for 30 minutes, protein was precipitated by the addition of 165 µl of chilled 50% (w/v) trichloroacetic acid (TCA). The precipitate was allowed to stand on ice for 5 minutes and then pelleted by centrifugation for 4 minutes at 13,000×$g_{max}$ (Eppendorf centrifuge). The pellet was washed once with 1 ml of 80% (v/v) acetone and briefly dried in vacuo. All reagent solutions and water needed for the tryptic digest were passed through a 0.45 µm filter (Ultrafree-MC, IVlillipore Products, Bedford, Mass.) prior to use. The pellet of the denatured protein (5 mg; 185 nmol) was dissolved in 90 µl of 0.8M ammonium bicarbonate, containing 8M urea. This solution was slowly diluted with 360 µl of water and then passed by centrifugation through a 0.45 µm filter. Subsequent steps were carried out in 0.5-ml siliconized microtubes (Phenix Research Products, Hayward, Calif.). An aliquot of 300 µl was mixed with 13 µl of 2.5 mg-ml$^{-1}$ trypsin in 1 mM HCl (mass ratio of BLAP:trypsin =100:1). As a control, 100 µl of the protein solution was mixed with 4.5 µl of 1 mM HCl. The remaining 50 µl aliquot of protein solution was mixed with 5 µl of 10% (v/v) trifluoroacetic acid (TFA) and used as control of the starting material. The two other solutions were incubated for 10 minutes at 37° C. The reactions were terminated by adding 30 µl and 10 µl of 10% (v/v) TFA to the digest and the control, respectively. The peptide mixture was separated by reverse-phase HPLC The HPLC equipment was from Waters (Milford, Mass.) and consisted of an autosampler (model 715 Ultra Wisp), a dual pump system (model 600E) and a diode array detector (model 990). Sampling and gradient formation was governed by Waters' software program '990$^+$ Powerline'. Tryptic peptides were separated on a C$_{18}$ column (Vydac model 218TP54; 4.6×250 mm; 5µ particle size; 300 Å pore size). In line with the separation column was a C$_{18}$ guard column (Vydac model 218FSK104, 10µ particle size). Separation column and guard column were housed in a column heater set to 30°±1° C. The solvent system used was: Solvent A=0.1% (v/v) TFA in water; Solvent B=0.08% (v/v) TFA in acetonitrile. After sample loading the C$_{18}$ column was developed for 3 minutes with Solvent A followed by a gradient from 0 to 35% (v/v) of Solvent B in Solvent A in 70 minutes. At 70 minutes the gradient increased to 100% Solvent B in 15 minutes and then returned to 100% Solvent A in 15 minutes. Prior to the next injection, the column was equilibrated for at least 20 minutes with Solvent A. Absorbance changes were recorded at 215 run and at 280 nm. Quantities of peptides mixtures separated for analytical and preparative purposes ranged from 11 µg (0.4 nmol) to 500 µg (18 nmol) in a volume of 5 to 50 µl at concentrations from 2.2 to 10 mg.ml$^{-1}$.

We claim:

1. A DNA sequence which controls the expression of a target gene, which extends from nucleotide 1 to nucleotide 312 as shown in FIG. 24 (Seq. ID 8) and which includes the ATCC 53926 alkaline protease promoter region, modified stemloop region, ribosomal binding site, initiation codon and the pre region of the 53296 alkaline protease gene, where the stem-loop region has been modified by deleting at least one base between nucleotide 161 and 203 on the ATCC 53926 DNA sequence as shown in FIGS. 2 and 24 (Seq. ID No. 8).

2. The DNA sequence of claim 1 which contains ATCC 53296 alkaline protease controlling element DNA sequence designated (P1) (Seq. ID No. 2).

3. The DNA sequence according to claim 2 joined to a target gene sequence encoding the pro and mature regions of a target protein.

4. A plasmid adapted to replicate in Bacillus which carries the DNA sequence defined in claim 3.

5. A plasmid adapted to replicate in Bacillus which carries the DNA sequence defined in claim 2.

6. The DNA sequence of claim 1 which contains ATCC 53296 alkaline protease controlling element DNA sequence designated (P2) (Seq. ID No. 3).

7. The DNA sequence according to claim 6 joined to a target gene sequence encoding the pro and mature regions of a target protein.

8. A plasmid adapted to replicate in Bacillus which carries the DNA sequence defined in claim 7.

9. A plasmid adapted to replicate in Bacillus which carries the DNA sequence defined in claim 6.

10. The DNA sequence of claim 1 which contains ATCC 53296 alkaline protease controlling element DNA sequence designated (P3) (Seq. ID No. 4.).

11. The DNA sequence according to claim 10 joined to a target gene sequence encoding the pro and mature regions of a target protein.

12. A plasmid adapted to replicate in Bacillus which carries the DNA sequence defined in claim 11.

13. A plasmid adapted to replicate in Bacillus which carries the DNA sequence defined in claim 10.

14. The DNA sequence of claim 1 which contains ATCC 53296 alkaline protease controlling element DNA sequence designated (P4) (Seq. ID No. 5).

15. The DNA sequence according to claim 14 joined to a target gene sequence encoding the pro and mature regions of a target protein.

16. A plasmid adapted to replicate in Bacillus which carries the DNA sequence defined in claim 15.

17. A plasmid adapted to replicate in Bacillus which carries the DNA sequence defined in claim 14.

18. The DNA sequence of claim 1 which contains ATCC 53296 alkaline protease controlling element DNA sequence designated (P5) (Seq. ID No. 6).

19. The DNA sequence according to claim 18 joined to a target gene sequence encoding the pro and mature regions of a target protein.

20. A plasmid adapted to replicate in Bacillus which carries the DNA sequence defined in claim 19.

21. A plasmid adapted to replicate in Bacillus which carries the DNA sequence defined in claim 18.

22. The DNA sequence according to claim 1 joined to a target gene sequence encoding the pro and mature regions of a target protein.

23. The DNA sequence of claim 22 in which the target gene sequence encodes the pro and mature regions of at least one hydrolytic enzyme.

24. A plasmid adapted to replicate in Bacillus which carries the DNA sequence defined in claim 23.

25. A DNA sequence according to claim 23 wherein the at least one the hydrolytic enzyme is a hydrolase selected from the group consisting of proteases, lipases and esterases.

26. A DNA sequence according to claim 23 wherein the at least one hydrolytic enzyme is a polysaccharide degrading enzyme selected from the group consisting of cellulases and amylases.

27. The DNA sequence of claim 22 in which the target gene sequence encodes the last four residues of the pre sequence and all of the pro and mature region of the *Bacillus lentus* alkaline protease.

28. A plasmid adapted to replicate in Bacillus which carries the DNA sequence defined in claim 27.

29. A plasmid adapted to replicate in Bacillus which carries the DNA sequence defined in claim 22.

30. A plasmid adapted to replicate in Bacillus which carries the DNA sequence defined in claim 1.

31. A plasmid as described in claim 30 for strains of *Bacillus subtilis*, the plasmid selected from the group consisting of pCB75C-P2, pCB75C-P3, pCB75C-P4, PCB76C-P2, and pCB76C-P3.

32. A Bacillus host transformed with at least one hybrid plasmid as described in claim 31.

33. A plasmid of claim 30 preferred for strains of *Bacillus subtills*, the plasmid selected from the group consisting of pCB56C-P1, pCB56C-P2, pCB56C-P3, PCB56C-P4, and pCB56C-P5.

34. A Bacillus host transformed with at least one hybrid plasmid as described in claim 33.

35. A Bacillus host transformed with at least one hybrid plasmid as described in claim 30.

36. The transformed Bacillus host of claim 35 wherein said host is *Bacillus licheniformis* ATCC 53926.

37. The transformed Bacillus host of claim 35 wherein said host is *Bacillus subtilis*.

38. A DNA sequence comprising a stem loop portion having a DNA sequence selected from the group consisting of Seq. ID No. 2, Seq. ID No. 3, Seq. ID No. 4, Seq. ID No. 5, and Seq. ID No. 6.

* * * * *

UNITED STATES PATENT AND TRADEMARK OFFICE
CERTIFICATE OF CORRECTION

PATENT NO. : 5,646,044
DATED : July 8, 1997
INVENTOR(S) : Wilson et al.

It is certified that error appears in the above-indentified patent and that said Letters Patent is hereby corrected as shown below:

In claim 1, line 13, "53296" should read --53926--.
In claim 2, line 19, "53296" should read --53926--.
In claim 6, line 29, "53296" should read --53926--.
In claim 10, line 39, "53296" should read --53926--.
In claim 14, line 49, "53296" should read --53926--.
In claim 18, line 59, "53296" should read --53926--.

Signed and Sealed this

Second Day of December, 1997

Attest:

BRUCE LEHMAN

Attesting Officer

Commissioner of Patents and Trademarks

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 85 base pairs
        ( B ) TYPE: nucleic acid
        ( C ) STRANDEDNESS: double
        ( D ) TOPOLOGY: linear ( i i ) MOLECULE TYPE: other nucleic acid
        ( A ) DESCRIPTION: /desc ="Partial DNA sequence of
            upstream region of native alkakine protease from strain
            ATCC 53926"

( v i ) ORIGINAL SOURCE:
        ( A ) ORGANISM: Bacillus licheniformis
        ( B ) STRAIN: ATCC 53926

( i x ) FEATURE:
        ( A ) NAME/KEY: stem_loop
        ( B ) LOCATION: 12..59

( x i ) SEQUENCE DESCRIPTION: SEQ ID NO:1:

```
TAATAAATTA ACAGAATAAT TGGAATAGAT TATATTATCC TTCTATTTAA ATTATTCTGA    60

ATAAAGAGGA GGAGAGTGAG TAATG                                         85
```

( 2 ) INFORMATION FOR SEQ ID NO:2:

( i ) SEQUENCE CHARACTERISTICS:
        ( A ) LENGTH: 72 base pairs
        ( B ) TYPE: nucleic acid
        ( C ) STRANDEDNESS: double
        ( D ) TOPOLOGY: linear ( i i ) MOLECULE TYPE: other nucleic acid
        ( A ) DESCRIPTION: /desc ="Partial DNA sequence of
            modified upstream region of alkaline protease gene from
            strain ATCC 53926"

( v i ) ORIGINAL SOURCE:
        ( A ) ORGANISM: Bacillus licheniformis
        ( B ) STRAIN: ATCC 53926

( v i i ) IMMEDIATE SOURCE:
        ( B ) CLONE: P1

( i x ) FEATURE:
        ( A ) NAME/KEY: stem_loop
        ( B ) LOCATION: 22..40

( x i ) SEQUENCE DESCRIPTION: SEQ ID NO:2:

```
TAATAAATTA ACAGAATAAT TGGAATAGAT TATATTATCC TTCTAGAATA TAGAGGAGGA    60

GAGTGAGTAA TG                                                       72
```

( 2 ) INFORMATION FOR SEQ ID NO:3:

( i ) SEQUENCE CHARACTERISTICS:
        ( A ) LENGTH: 55 base pairs
        ( B ) TYPE: nucleic acid
        ( C ) STRANDEDNESS: double
        ( D ) TOPOLOGY: linear ( i i ) MOLECULE TYPE: other nucleic acid
        ( A ) DESCRIPTION: /desc ="Partial DNA sequence of
            modified upstream region of alkaline protease gene from
            strain ATCC 53926"

(v i) ORIGINAL SOURCE:
    (A) ORGANISM: Bacillus licheniformis
    (B) STRAIN: ATCC 53926

(v i i) IMMEDIATE SOURCE:
    (B) CLONE: P2

(i x) FEATURE:
    (A) NAME/KEY: stem_loop
    (B) LOCATION: 11..28

(x i) SEQUENCE DESCRIPTION: SEQ ID NO:3:

TAATAAATTA ACAGAATAAT TGGATCCTGA ATAAGAGGA GGAGAGTGAG TAATG    55

(2) INFORMATION FOR SEQ ID NO:4:

(i) SEQUENCE CHARACTERISTICS:
    (A) LENGTH: 72 base pairs
    (B) TYPE: nucleic acid
    (C) STRANDEDNESS: double
    (D) TOPOLOGY: linear (i i) MOLECULE TYPE: other nucleic acid
    (A) DESCRIPTION: /desc ="Partial DNA sequence of
        modified upstream region of alkaline protease gene from
        strain ATCC 53926"

(v i) ORIGINAL SOURCE:
    (A) ORGANISM: Bacillus licheniformis
    (B) STRAIN: ATCC 53926

(v i i) IMMEDIATE SOURCE:
    (B) CLONE: P3

(i x) FEATURE:
    (A) NAME/KEY: stem_loop
    (B) LOCATION: 12..46

(x i) SEQUENCE DESCRIPTION: SEQ ID NO:4:

TAATAAATTA ACAGAATAAT TGGATCCTTC TATTTAAATT ATTCTGAATA AAGAGGAGGA    60

GAGTGAGTAA TG    72

(2) INFORMATION FOR SEQ ID NO:5:

(i) SEQUENCE CHARACTERISTICS:
    (A) LENGTH: 46 base pairs
    (B) TYPE: nucleic acid
    (C) STRANDEDNESS: double
    (D) TOPOLOGY: linear (i i) MOLECULE TYPE: other nucleic acid
    (A) DESCRIPTION: /desc ="Partial DNA sequence of
        modified upstream region of alkaline protease gene from
        strain ATCC 53926"

(v i) ORIGINAL SOURCE:
    (A) ORGANISM: Bacillus licheniformis
    (B) STRAIN: ATCC 53926

(v i i) IMMEDIATE SOURCE:
    (B) CLONE: P4

(i x) FEATURE:
    (A) NAME/KEY: stem_loop
    (B) LOCATION: 12..20

(x i) SEQUENCE DESCRIPTION: SEQ ID NO:5:

TAATAAATTA ACAGATCCTG AATAAGAGG AGGAGAGTGA GTAATG    46

(2) INFORMATION FOR SEQ ID NO:6:

(i) SEQUENCE CHARACTERISTICS:
    (A) LENGTH: 63 base pairs (B) TYPE: nucleic acid
(C) STRANDEDNESS: double
(D) TOPOLOGY: linear (ii) MOLECULE TYPE: other nucleic acid
(A) DESCRIPTION: /desc ="Partial DNA sequence of
modified upstream region of alkaline protease from
strain ATCC 53926"

(vi) ORIGINAL SOURCE:
(A) ORGANISM: Bacillus licheniformis
(B) STRAIN: ATCC 53926

(vii) IMMEDIATE SOURCE:
(B) CLONE: P5

(ix) FEATURE:
(A) NAME/KEY: stem_loop
(B) LOCATION: 12..37

(xi) SEQUENCE DESCRIPTION: SEQ ID NO:6:

| | | | | | | |
|---|---|---|---|---|---|---|
| TAATAAATTA | ACAGATCCTT | CTATTTAAAT | TATTCTGAAT | AAAGAGGAGG | AGAGTGAGTA | 60 |
| ATG | | | | | | 63 |

(2) INFORMATION FOR SEQ ID NO:7:

(i) SEQUENCE CHARACTERISTICS:
(A) LENGTH: 655 base pairs
(B) TYPE: nucleic acid
(C) STRANDEDNESS: double
(D) TOPOLOGY: linear (ii) MOLECULE TYPE: other nucleic acid
(A) DESCRIPTION: /desc ="Partial DNA sequence of
ATCC 53926:BLAP ClaI fusion gene"

(vi) ORIGINAL SOURCE:
(A) ORGANISM: Bacillus licheniformis
(B) STRAIN: ATCC 53926

(xi) SEQUENCE DESCRIPTION: SEQ ID NO:7:

| | | | | | | |
|---|---|---|---|---|---|---|
| CTCGGGACCT | CTTTCCCTGC | CAGGCTGAAG | CGGTCTATTC | ATACTTTCGA | ACTGAACATT | 60 |
| TTTCTAAAAC | AGTTATTAAT | AACCAAAAAA | TTTTAAATTG | GTCCTCCAAA | AAAATAGGCC | 120 |
| TACCATATAA | TTCATTTTTT | TTCTATAATA | AATTAACAGA | ATAATTGGAA | TAGATTATAT | 180 |
| TATCCTTCTA | TTTAAATTAT | TCTGAATAAA | GAGGAGGAGA | GTGAGTAATG | ATGAGGAAAA | 240 |
| AGAGTTTTTG | GCTTGGGATG | CTGACGGCCT | TCATGCTCGT | GTTCACGATG | GCATCGATCG | 300 |
| CATCGGCTGC | TGAGGAAGCA | AAAGAAAAAT | ATTTAATTGG | CTTTAATGAG | CAGGAAGCTG | 360 |
| TCAGTGAGTT | TGTAGAACAA | GTAGAGGCAA | ATGACGAGGT | CGCCATTCTC | TCTGAGGAAG | 420 |
| AGGAAGTCGA | AATTGAATTG | CTTCATGAGT | TTGAAACGAT | TCCTGTTTTA | TCCGTTGAGT | 480 |
| TAAGCCCAGA | AGATGTGGAC | GCGCTTGAAC | TTGATCCAGC | GATTCTTAT | ATTGAAGAGG | 540 |
| ATGCAGAAGT | AACGACAATG | GCGCAATCAG | TGCCATGGGG | AATTAGCCGT | GTGCAAGCCC | 600 |
| CGGCTGCCCA | TAACCGTGGA | TTGACAGGTT | CTGGTGTAAA | AGTTGCTGTC | CTCGA | 655 |

(2) INFORMATION FOR SEQ ID NO:8:

(i) SEQUENCE CHARACTERISTICS:
(A) LENGTH: 1452 base pairs
(B) TYPE: nucleic acid
(C) STRANDEDNESS: double
(D) TOPOLOGY: linear (ii) MOLECULE TYPE: other nucleic acid
(A) DESCRIPTION: /desc ="DNA sequence of the
alkaline protease gene of strain ATCC 53926 and its
controlling elements"

( v i ) ORIGINAL SOURCE:
    ( A ) ORGANISM: Bacillus licheniformis
    ( B ) STRAIN: ATCC 53926

( x i ) SEQUENCE DESCRIPTION: SEQ ID NO:8:

```
CCTCGGGACC  TCTTTCCCTG  CCAGGCTGAA  GCGGTCTATT  CATACTTTCG  AACTGAACAT    60
TTTTCTAAAA  CAGTTATTAA  TAACCAAAAA  ATTTTAAATT  GGTCCTCCAA  AAAAATAGGC   120
CTACCATATA  ATTCATTTTT  TTTCTATAAT  AAATTAACAG  AATAATTGGA  ATAGATTATA   180
TTATCCTTCT  ATTTAAATTA  TTCTGAATAA  AGAGGAGGAG  AGTGAGTAAT  GATGAGGAAA   240
AAGAGTTTTT  GGCTTGGGAT  GCTGACGGCC  TTCATGCTCG  TGTTCACGAT  GGCATTCAGC   300
GATTCCGCTT  CTGCTGCTCA  ACCGGCGAAA  AATGTTGAAA  AGGATTATAT  TGTCGGATTT   360
AAGTCAGGAG  TGAAAACCGC  ATCTGTCAAA  AAGGACATCA  TCAAAGAGAG  CGGCGGAAAA   420
GTGGACAAGC  AGTTTAGAAT  CATCAACGCG  GCAAAAGCGA  AGCTAGACAA  AGAAGCGCTT   480
AAGGAAGTCA  AAAATGATCC  GGATGTCGCT  TATGTGGAAG  AGGATCATGT  GGCCCATGCC   540
TTGGCGCAAA  CCGTTCCTTA  CGGCATTCCT  CTCATTAAAG  CGGACAAAGT  GCAGGCTCAA   600
GGCTTTAAGG  GAGCGAATGT  AAAAGTAGCC  GTCCTGGATA  CAGGAATCCA  AGCTTCTCAT   660
CCGGACTTGA  ACGTAGTCGG  CGGAGCAAGC  TTTGTGGCTG  GCGAAGCTTA  TAACACCGAC   720
GGCAACGGAC  ACGGCACACA  TGTTGCCGGT  ACAGTAGCTG  CGCTTGACAA  TACAACGGGT   780
GTATTAGGCG  TTGCGCCAAG  CGTATCCTTG  TACGCGGTTA  AAGTACTGAA  TTCAAGCGGA   840
AGCGGATCAT  ACAGCGGCAT  TGTAAGCGGA  ATCGAGTGGG  CGACAACAAA  CGGCATGGAT   900
GTTATCAATA  TGAGCCTTGG  GGGAGCATCA  GGCTCGACAG  CGATGAAACA  GGCAGTCGAC   960
AATGCATATG  CAAGAGGGGT  TGTCGTTGTA  GCTGCAGCAG  GGAACAGCGG  ATCTTCAGGA  1020
AACACGAATA  CAATTGGCTA  TCCTGCAAAA  TACGATTCTG  TCATCGCTGT  TGGTGCGGTA  1080
GACTCTAACA  GCAACAGAGC  TTCATTTTCC  AGCGTCGGAG  CAGAGCTTGA  AGTCATGGCT  1140
CCTGGCGCAG  GCGTATACAG  CACTTACCCA  ACGAACACTT  ATGCAACATT  GAACGGAACG  1200
TCAATGGCTT  CTCCTCATGT  AGCGGGAGCA  GCAGCTTTGA  TCTTGTCAAA  ACATCCGAAC  1260
CTTTCAGCTT  CACAAGTCCG  CAACCGTCTC  TCCAGCACGG  CGACTTATTT  GGGAAGCTCC  1320
TTCTACTATG  GGAAAGGTCT  GATCAATGTC  GAAGCTGCCG  CTCAATAACA  TATTCTAACA  1380
AATAGCATAT  AGAAAAAGCT  AGTGTTTTA   GCACTAGCTT  TTTCTTCATT  CTGATGAAGG  1440
TTGTTCAATA  TT                                                          1452
```

( 2 ) INFORMATION FOR SEQ ID NO:9:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note="N-SUCCINYL"

( i x ) FEATURE:
        ( A ) NAME/KEY: Modified-site
        ( B ) LOCATION: 4
        ( D ) OTHER INFORMATION: /note=
            " P-NITROANILIDE"

( x i ) SEQUENCE DESCRIPTION: SEQ ID NO:9:

Ala Ala Pro Phe                                                           4